US010987302B2

United States Patent
Walther et al.

(10) Patent No.: US 10,987,302 B2
(45) Date of Patent: *Apr. 27, 2021

(54) METHODS FOR THE PRODUCTION OF A COSMETIC COMPOSITION FROM HATCHING FLUID AND USES THEREOF FOR IMPROVING THE COSMETIC APPEARANCE OF SKIN

(71) Applicants: Bernt Th. Walther, Bergen (NO); Hans Kristian Leren, Bergen (NO)

(72) Inventors: Bernt Th. Walther, Bergen (NO); Hans Kristian Leren, Bergen (NO)

(73) Assignee: AQUA BIO TECHNOLOGY ASA, Bergen (NO)

(*) Notice: Subject to any disclaimer, the term of this patent is extended or adjusted under 35 U.S.C. 154(b) by 0 days.

This patent is subject to a terminal disclaimer.

(21) Appl. No.: 16/440,361

(22) Filed: Jun. 13, 2019

(65) Prior Publication Data

US 2019/0350837 A1    Nov. 21, 2019

Related U.S. Application Data

(62) Division of application No. 14/128,810, filed as application No. PCT/EP2012/062253 on Jun. 25, 2012, now Pat. No. 10,328,021.

(30) Foreign Application Priority Data

Jun. 24, 2011 (GB) ..................... 1110783

(51) Int. Cl.
| | | |
|---|---|---|
| *A61K 8/64* | (2006.01) | |
| *A61K 38/17* | (2006.01) | |
| *C07K 1/34* | (2006.01) | |
| *A61K 35/60* | (2006.01) | |
| *A61Q 19/08* | (2006.01) | |
| *A61K 8/98* | (2006.01) | |
| *A61Q 19/00* | (2006.01) | |
| *C07K 14/46* | (2006.01) | |
| *A61Q 19/02* | (2006.01) | |

(52) U.S. Cl.
CPC .............. *A61K 8/987* (2013.01); *A61K 8/64* (2013.01); *A61K 35/60* (2013.01); *A61K 38/1706* (2013.01); *A61Q 19/007* (2013.01); *A61Q 19/02* (2013.01); *A61Q 19/08* (2013.01); *C07K 1/34* (2013.01); *C07K 14/461* (2013.01)

(58) Field of Classification Search
None
See application file for complete search history.

(56) References Cited

U.S. PATENT DOCUMENTS

| 6,899,863 | B1 | 5/2005 | Dhellin et al. |
| 2008/0038300 | A1 | 2/2008 | Jaspers et al. |
| 2009/0043236 | A1 | 2/2009 | Kawamura et al. |
| 2009/0274770 | A1 | 11/2009 | Gammelsaeter et al. |
| 2012/0309689 | A1 | 12/2012 | Leren et al. |
| 2014/0220088 | A1 | 8/2014 | Walther et al. |

FOREIGN PATENT DOCUMENTS

| DE | 10001740 | 7/2001 |
| JP | 2002-535665 | 10/2002 |
| JP | 2003-511093 | 3/2003 |
| JP | 2008-520651 | 6/2006 |
| WO | 99/29836 | 6/1999 |
| WO | 01/28353 | 4/2001 |
| WO | 2005/067499 | 7/2005 |
| WO | 2006/054309 | 5/2006 |
| WO | 2009/085302 | 7/2009 |
| WO | 10/049688 | 5/2010 |
| WO | 11/064384 | 6/2011 |

OTHER PUBLICATIONS

International Search Report and Written Opinion for PCT/EP2012/062253, dated Jun. 14, 2013.
Hagenmaier et al: The hatching process in fish embryos. IV. The enzymological properties of a highly purified enzyme (chorionase) from the hatching fluid of the rainbow trout, *Salmo gairdneririch.* Comp. Biochem. Physiol. 1974. 49(2):313-324.
Oppen-Berntsen, D. et al., The Effects of Hypoxia, Alkalinity and Neurochemicals on Hatching of Atlantic Salmon (*Salmo salar*) Eggs, Aquaculture, 86 (1990) 417-430.
Oppen-Berntsen D. et al. Eggshell zona radiata proteins from cod (*Gadus morhua*): extra-ovarian origin and induction by estradiol-17 beta. Int J Dev Biol. 1992 36(2):247-54.
Pitman (Aqua Bio rebrands main ingredients after study proves anti-ageing function, Cosmetics design-europe.com, p. 1, published on Mar. 2, 2011).
Houp (Ultrafiltration and Diafiltration, J. Validation Tech. 2009, pp. 40-46.
EtsEQ Membrane separations, 2003, slide 1-7, http://www.etseq.urv.es/doctorat/index/running/2003_2005/courses_w/memb_sep/Memb07.pdf.
Office Action dated Mar. 2, 2016, in corresponding Chinese application No. 201280031250.0 with English translation.
Office Action dated Feb. 25, 2016, in corresponding Japanese application No. 2014-516389 with English translation.
Press release for Zonase X™, by Aqua Bio Technology AS, Oslo, Norway, dated Mar. 30, 2010.

(Continued)

*Primary Examiner* — Kevin S Orwig
(74) *Attorney, Agent, or Firm* — Wenderoth, Lind & Ponack, L.L.P.

(57) ABSTRACT

The present invention relates to cosmetic compositions obtained or obtainable from Salmonidae hatching fluid, methods of producing said compositions and their use in various cosmetic applications to the skin, particularly for reducing or preventing the cosmetic appearance or prevalence of wrinkles, fine lines, hyperpigmentation, laxity, dry skin, scaling and/or transepidermal water loss in skin of a mammalian animal.

20 Claims, 7 Drawing Sheets

(56) References Cited

OTHER PUBLICATIONS

First sale of Zonase X™ by Aqua Bin Technology AS, Oslo, Norway, occurred on Oct. 17, 2010.
Product brochure for Aquabeautine XL®, by Aqua Bio Technology AS, Oslo, Norway, dated Dec. 2011.
First sale of Aquabeautine XL® Aqua Bio Technology AS, Oslo, Norway, occurred after May 3, 2011.

METHODS FOR THE PRODUCTION OF A COSMETIC COMPOSITION FROM HATCHING FLUID AND USES THEREOF FOR IMPROVING THE COSMETIC APPEARANCE OF SKIN

The present invention relates to the use of a composition comprising polypeptides or portions of polypeptides, which is derivable from Salmonidae hatching fluid, in various applications to the skin. In particular, the composition is useful for altering, preferably improving, the cosmetic appearance of aged skin.

The skin is one of the more vulnerable organs of the body. Skin is in constant interaction with external stimuli, directly or indirectly, and is frequently exposed to, and affected by, environmental agents. In fact, the skin can be seen as the first point of contact with the outside world. This constant exposure can result in unpleasant and/or unwanted physical and visible changes to the skin, particularly to the cosmetic appearance of skin. Whilst such changes may not threaten the health of an individual, such changes may be physically uncomfortable or visibly disagreeable. Indeed, because the skin is so visible, changes to the appearance of skin can lead to psychological stress. There is therefore a continuing need and demand for effective treatments to maintain, restore or improve the condition of the skin, and in particular to restore the youthful appearance of skin.

Skin forms the largest organ of the body, accounting for about 12-16 percent of a person's weight. It performs many vital roles as both a barrier and a regulating influence between the outside world and the controlled environment within our bodies.

Skin consists of 3 layers, namely the epidermis, dermis and subcutis. The epidermis is the uppermost, epithelial layer of the skin. It acts as a physical barrier, preventing loss of water from the body, and preventing entry of substances and organisms into the body. Its thickness varies according to body site.

The epidermis consists of stratified squamous epithelium, i.e. it consists of layers of flattened cells. Skin, hair and nails are keratinised, meaning they have a dead, hardened hydrophobic surface made of a protein called keratin. Epidermis is made impermeable due to its contents of extracellular lipids associated with keratinocytes, especially in the middle layer of the epidermis (stratum lucidum). Mucous membranes (e.g. of the oesophagus, oral pharyngeal cavity, reproductive organs, and others) are mainly non-keratinised and moist. The epidermis has three main types of cell, namely keratinocytes (skin cells), melanocytes (pigment-producing cells) and Langerhans cells (immune cells). The Merkel cell is a fourth, less prevalent, epidermal cell.

The keratinocytes mature and differentiate with accumulation of keratin as they move outwards. They eventually fall or rub off. They form four or five distinct strata, which from the most superficial to the deepest are (i) the Stratum corneum (horny layer) with dead, dried-out hard cells without nuclei, (ii) the Stratum granulosum (granular layer) with cells containing basophilic granules and outwardly separated from stratum corneum by the thin stratum lucidum, (iii) the Stratum spinulosum (spinous, spiny or prickle cell layer) in which the cells become increasingly flattened as they move upward and (iv) the Stratum basale (basal layer) with columnar (tall) regenerative cells.

Immediately below the epidermis is the basement membrane, a specialised structure that lies between the epidermis and dermis.

The dermis is the fibrous connective tissue or supportive layer of the skin. The major fibres are collagen fibres and elastin which are interwoven.

The subcutis is the fat layer immediately below the dermis and epidermis. It is also called subcutaneous tissue, hypodermis or panniculus. The subcutis mainly consists of fat cells (adipocytes), nerves and blood vessels.

New epithelial skin cells are created in the skin's lower layer, the stratum granulosum. Over time, cells migrate to the surface of the skin and become more acidic. During their 30 day journey, they die and become saturated with keratin. Keratin and associated lipids are important because they protect the skin from outside elements.

Many factors may contribute to the deterioration in the cosmetic appearance of skin including disease, injury, environmental factors, age, hormone levels, medication, externally applied or ingested materials, genetic conditions or a combination of these and other factors. Age related deterioration in the cosmetic appearance of skin is a universal factor, particularly photoageing, i.e. Dermatoheliosis. This deterioration can be seen in irregularities or abnormalities in the skin, which may appear as, e.g. dry skin, wrinkles, fine lines, increased laxity (sagging) or altered pigmentation.

Photoageing is a term used for the characteristic changes induced by chronic UVA and UVB exposure. The deterioration of biological functions and ability to manage metabolic stress is one of the major consequences of the ageing process. Ageing is a complex, progressive process which also leads to functional and aesthetic changes in the skin.

Photoageing is a process of ageing of the skin attributed to continuous, long-term exposure of skin to ultraviolet (UV) radiation of approximately 245-290 nm, which may be from natural or synthetic light. Photoageing is thus also known as ageing of the skin, particularly of the face, ears, neck and hands, caused by UVA and UVB rays.

Dry and/or scaling skin is one of the most common signs of ageing skin. Although certain individuals are more susceptible to dry and/or scaling skin, the appearance of dry and/or scaling skin can affect anyone, regardless of age, gender, or skin type.

Dry skin occurs when the skin's outer layer (the stratum corneum with the stratum lucidum) is depleted of water, i.e. via trans-epidermal water loss (TEWL). When this layer is well-moistened, it minimizes water loss through the skin and helps keep out irritants, allergens, and germs. However, when the stratum corneum dries out, its protective function is reduced. This allows greater water loss, leaving skin vulnerable to environmental factors.

Ideally the stratum corneum has a water content of 10% to 30%. This water imparts to the skin its soft, smooth, and flexible texture, i.e. the characteristics associated with the youthful appearance of skin. The water comes from the atmosphere, the underlying layers of skin, and sweat. Oil produced by skin glands and fatty substances produced by skin cells act as natural moisturizers, allowing the stratum corneum to seal in water.

The body continuously loses water from the skin's surface by evaporation (TEWL). Under normal conditions, the rate of loss is slow, and the water is adequately replaced. Characteristic signs and symptoms of dry skin occur when the water loss exceeds the water replacement, and the stratum corneum's water content falls below 10%.

Moisturizers which improve or eradicate dry and/or scaling skin, thereby improving the cosmetic appearance of skin, are highly desirable. Whilst many moisturizers are known in the art, there remains a need for natural products which are effective yet gentle.

Epidermal cells exhibiting a undesired or excessive pigmentation, i.e. hyper-pigmentation, e.g. liver spots, is another common sign of ageing skin. Traditionally exfoliation may be used to remove epidermal cells that are detrimental to the cosmetic appearance of skin.

Exfoliation removes the outer strata of epidermis to reveal the newer skin cells beneath. Exfoliation may be achieved by physical means (i.e. abrasion of the skin) or by chemical means. Chemical exfoliants include scrubs containing salicylic acid, glycolic acid, fruit enzymes, citric acid or malic acid and may be applied in high concentrations by a dermatologist, or in lower concentrations in over-the-counter products. Chemical exfoliation may involve the use of products that contain alpha hydroxy acids (AHAs) or beta hydroxy acids (BHAs), or enzymes that act to loosen the glue-like substances that hold the cells together at cell junctions, allowing them to ease away. This type of exfoliation is recommended for people treating acne.

The greatest disadvantage to exfoliation is the high price of some of the products and methods used to achieve it. Exfoliation will lead to some initial redness to the skin. Near the end of chemical peels, the skin will frost, with colours varying from a bright white to gray on the skin surface.

Hence, effective methods to reduce hyperpigmentation of skin, which are gentler on the skin than exfoliation, are therefore desirable.

There thus remains a need for treatments suitable for promoting the aesthetic appearance of skin. In other words, methods of improving the cosmetic appearance of skin are desirable. In particular, there is a demand for methods for restoring the youthful appearance to aged skin and/or combating the signs of ageing skin.

A composition comprising molecules, namely polypeptides or portions of polypeptides, which are found in Salmonidae hatching fluid have surprisingly now been found to be remarkably effective at improving the cosmetic appearance of skin, particularly reducing the physical signs or symptoms associated with ageing skin.

Hatching of fish embryos is achieved by various enzymes, known as hatching enzymes, which are capable of degrading the proteinaceous eggshell. Oocytes of all vertebrates have characteristic extracellular envelopes, known as vitelline envelopes, eggshells or chorion, which are made up by the cross-linkage of various polypeptides. Proteases with different specificities act on the chorion to breakdown the eggshell and facilitate the release of the fish embryo. Hence, the fluid in which the embryo hatches comprises a multitude of polypeptides and portions of polypeptides, i.e. degradation products.

Compositions comprising proteins and portions of polypeptides, which are derived from Salmonidae hatching fluid have surprisingly been found to have pronounced effects on the cosmetic appearance of skin. Whilst not wishing to be bound by theory, the Examples demonstrate that compositions comprising Salmonidae hatching fluid polypeptides and portions of polypeptides are capable of restoring the youthful appearance of skin. It is thought that the combination of polypeptides and portions of polypeptides in the compositions defined herein (which are thought to comprise at least 50 different polypeptides or portions of polypeptides) may interact with different types of proteins present in the dermis and epidermis of the skin. It is believed that the combination of polypeptides and portions of polypeptides may work in synergy and that these interactions may be, at least in part, responsible for the effects of the composition on the cosmetic/aesthetic appearance of the skin.

Accordingly, at its broadest, the invention can be seen to provide a composition comprising polypeptides and portions of polypeptides derivable from Salmonidae hatching fluid for use in, or in methods for, promoting the aesthetic appearance of skin. In other words, a composition comprising polypeptides and portions of polypeptides derivable from Salmonidae hatching fluid as described herein for use in, or in methods for, improving the cosmetic appearance of skin. In a particularly preferred aspect, the invention may be seen as providing a composition comprising polypeptides and portions of polypeptides derivable from Salmonidae hatching fluid as described herein for use in, or in methods for, restoring the youthful appearance to aged skin and/or combating the signs of ageing skin. The composition referred to above is also referred to herein as a "Salmonidae hatching fluid extract". In addition to polypeptides and portions of polypeptides, said extract may comprise native non-proteinaceous material.

It will be evident from the disclosures below that a composition comprising polypeptides and portions of polypeptides derivable from Salmonidae hatching fluid as described herein may be provided as a cosmetic composition, which comprises one or more pharmaceutically acceptable excipients and/or diluents.

Thus, in one aspect the present invention provides a method of preparing a cosmetic composition as described herein from Salmonidae hatching fluid (e.g. salmon hatching fluid) comprising at least the steps of:

a) suspending Salmonidae eggs in a minimal volume of water (e.g. equivalent to the volume of the eggs or less);

b) inducing synchronized, rapid hatching of said eggs (preferably such that hatching is complete within less than 2 hours for more than 95% of the embryos);

c) optionally filtering the hatched eggs to obtain hatching fluid; and d) filtering the hatching fluid to obtain the polypeptide and/or composition, wherein the step of filtering the hatching fluid comprises at least the steps of:

(i) filtering the hatching fluid using a filter with a pore size of at least 5 μm, preferably 5-15 μm, and particularly preferably a pore size of 7 μm, and collecting the filtrate;

(ii) filtering the filtrate from step (i) using a filter with a pore size of 0.30-0.60 μm, preferably a pore size of 0.35-0.55 μm, particularly preferably 0.40-0.50 μm, most preferably 0.45 μm, and collecting the filtrate;

(iii) exchanging the water in the filtrate from step (ii) with a pharmaceutically acceptable buffer;

(iv) filtering the solution obtained from step (iii) using a filter with a pore size of 0.15-0.30 μm, preferably a pore size of 0.22 μm and collecting the filtrate; and (v) preparing said cosmetic composition from the filtrate from step (iv).

The step of exchanging the water in the filtrate may be performed using any suitable method known in the art, e.g. diafiltration or dialysis. In a particularly preferred embodiment, this step is performed using diafiltration using a filter with an exclusion size of less than 15 kDa, preferably 10 kDa or less, e.g. 9, 8, 7, 6, 5, 4, 3 kDa or less.

Diafiltration uses ultrafiltration membranes to remove e.g. salts or other unwanted or undesirable microsolutes from a solution or as a way of exchanging the solvent, e.g. buffer, of a solution. Small molecules are separated from a solution while retaining larger molecules in the retentate (the material which does not pass through the filter). Microsolutes and solvents, e.g. water, are generally easily washed through the membrane. Typically about 3 volumes of diafiltration solvent will eliminate 95% of the microsolute. Thus, the above filtrate from step (ii) is initially processed by diafiltration and this results in the concentration of the retentate as a proportion of the solution (which contains the soluble impurities/unwanted fraction of the hatching fluid) passes through the membrane. The retentate is then diluted with a pharmaceutically acceptable buffer, e.g. 0.5 mM Sodium phosphate and 1 mM Sodium chloride, phosphate buffered saline etc. The diluted retentate may be subjected to repeated rounds of diafiltration, if necessary. Typically, prior to step (iv) the retentate is diluted such that the filtrate from step (iv) has an enzymatic activity of 3000-5000 mU/L, preferably 3000-4000 mU/L and most preferably about 3400 mU/L. The enzymatic activity of the filtrate may be measured by the capacity of the filtrate to cleave the Factor Xa chromogenic substrate ($CH_3OCO$-D-CHA-Gly-Arg-pNA-AcOH, Sigma aldrich product number: F3301-25MG). Prior to the step of diafiltration the hatching fluid may comprise an enzymatic activity in the range of 10 to 150,000 mU/L.

The Factor Xa chromogenic substrate (Sigma-Aldrich) is cleaved by an enzyme present in the hatching fluid yielding a yellow product that can be measured conveniently using spectrophotometrical analysis at a wavelength of 405 nm. A typical assay comprises the addition of 100 µl hatching fluid solution, obtainable from step (iii) of the above method, to 600 µl substrate solution, comprising 10 µl Factor Xa chromogenic substrate (10 mg/ml), 70 µl 0.2 M Tris-HCl pH 8.5 and 520 µl $dH_2O$. Conveniently the change in absorbance may be measured for 5-20 minutes, typically 10 minutes. The result is multiplied with an appropriate factor, e.g. 10 (for a 10 minute assay) to get the enzyme activity per 1 ml of sample. Other appropriate and equivalent substrates may be used to determine the activity of the hatching fluid.

Synchronized hatching may be achieved by any suitable method known in the art. For instance, eggs may be synchronized using photo-manipulation, e.g. transferring eggs from the light (which inhibits hatching) in to conditions with no light. Manipulation of the temperature of the solution, by deoxygenation (Oppen-Berntsen et al. 1990, Aquaculture, 86, pp. 417-430), and stimulation using electricity can also be used to cause synchronized hatching. As noted above, a minimal volume of water may be equivalent to the volume of eggs or less, e.g. for every 1 ml of eggs a suspending liquid of ≤1, 0.75, 0.5, 0.25 ml may be used, e.g. from 0.5 to 1 ml.

The method of preparing a cosmetic composition described above results in an enriched preparation which is preferably substantially free of any contaminating components derived from the source material or material used in the isolation procedure, e.g. components other than the polypeptides or portions of polypeptides comprised in the crude hatching fluid. In a preferred embodiment the composition may be enriched to a degree of purity of more than 30, 40, 50 or 60%, e.g. >70, 80 or 90%, purity as assessed w/w (dry weight) of the polypeptides and portions of polypeptides in comparison to the starting hatching fluid, i.e. 90% purity refers to a loss of 90% of the starting material (contaminating components) through the course of the method of preparation. However, compositions may be used which have lower purity, e.g. retain more than 40, 50, 60, 70, 80 or 90% of the starting material.

Whilst the filtrate may itself form the cosmetic composition, optionally the product (the filtrate of step (iv)) obtained or obtainable from the above method may be diluted (or concentrated) to an appropriate concentration prior to its use in the methods and uses of the invention. Thus, the method may comprise a further step of diluting (or concentrating) the composition. Preferably the filtrate may be diluted (or concentrated) by a factor of at least 1.5, 2, 3, 4, 5, 10, 15, 20, 50, 100, 1000, 5000 or 10000. In a particularly preferred embodiment, the solution from step (iii) of the above method is diluted or concentrated to achieve a solution with an enzymatic activity of 1000-10000 mU/L as measured by the above described method. Preferably the solution, and therefore the filtrate from step (iv) comprises an activity of 2000-10000, 3000-9000, 3000-7000, 3000-6000, 3000-5000 or 3000-4000 mU/L. Most preferably the solution comprises an activity of about 3400 mU/L.

Optionally, one or more pharmaceutically acceptable excipients and/or diluents may be added to the product obtained or obtainable from the above method. Thus, the method may comprise a further step of adding one or more pharmaceutically acceptable excipients and/or diluents to the composition or combining the composition with one or more pharmaceutically acceptable excipients and/or diluents. Alternative or additional preparation method steps include changing or modifying the solvent, e.g. pH, ion concentration etc.

Other pharmaceutically acceptable components or ingredients may be added to the product obtained or obtainable from the above method. The one or more other components may be active components, i.e. components that have an effect on the skin, preferably that also act to promote the aesthetic appearance of skin or improve the cosmetic appearance of skin, e.g. in the cosmetic indications described herein. Thus, alternatively or additionally, the method may comprise a further step of adding one or more pharmaceutically acceptable active components to the composition or combining the composition with one or more pharmaceutically acceptable active components. Pharmaceutically acceptable active components may include minerals, vitamins, enzymes, proteins, peptides, amino acids, lipids, antioxidants, polysaccharides, substances suitable as sunscreen filters, chemical exfoliants, extracts and mixtures thereof, as described in more detail below.

The cosmetic composition obtained or obtainable from the above methods is suitable for use in the methods of the invention, as described elsewhere herein. In particular, the cosmetic composition is for use in improving the cosmetic appearance of skin in a mammalian animal.

The invention also provides a method for improving the cosmetic appearance of skin of a mammalian animal wherein a cosmetic composition as defined above is administered to said animal.

A further aspect of the invention is the use of a cosmetic composition as defined above in the manufacture of a medicament for improving the cosmetic appearance of skin of a mammalian animal.

"Polypeptides" as referred to herein are molecules with preferably more than 50, 100, 150, 200 or 250 residues and/or less than 500, 400, 300, 200 or 100 residues or a range selected therefrom. As referred to herein a "portion" preferably comprises at least 30, 40, 50, 60, 70, 80, 90, 100, 110, 120, 130, 140, 150, 160, 170, 180, 190, 200, 210, 220, 230, 240 or more amino acids of the sequence from which it is derived. Said portion may be obtained from a central or N-terminal or C-terminal portions of the sequence.

The compositions as defined herein may be obtained from any Salmonidae eggs, which may be viewed as natural biological variations of the starting material. Particularly preferred Salmonidae eggs are those from the sub-families *Salmo* and *Oncorhynchus*. An especially preferred starting material for the method described above are eggs from Atlantic salmon (*Salmo salar*) or Pacific salmon (*Oncorhynchus masou*).

The cosmetic compositions described herein are for use in vivo as discussed herein.

By "pharmaceutically acceptable" or "physiologically acceptable" is meant that the ingredient must be suitable for cosmetic application and compositions. The ingredients also must be compatible with other ingredients in the composition as well as physiologically acceptable to the recipient.

The active ingredient, i.e. the composition obtainable by the method described above, for administration may be appropriately modified for use in a cosmetic composition. For example the composition used in accordance with the invention may be stabilized against degradation for example by the use of appropriate additives such as salts or non-electrolytes, acetate, SDS, EDTA, citrate or acetate buffers, mannitol, glycine, HSA or polysorbate.

The compositions obtained by the methods described herein may be present in the compositions for the cosmetic uses as the sole active ingredient or may be combined with other ingredients, particularly other active ingredients, e.g. to augment the cosmetic effect (as described above) or to make the composition more appealing to the consumer.

As mentioned above, the compositions described herein exhibit properties that are useful in improving the cosmetic appearance of skin, particularly of aged skin, e.g. photo-aged skin.

The composition described herein may also comprise impurities, e.g. after the preparation of said composition from one of the above described natural sources. In compositions as described herein, the various polypeptides or portions of polypeptides derivable from Salmonidae hatching fluid may be present (in combination) in the range 0.0001 to 50% w/w of the cosmetic composition prepared according to the above described method. Preferably said polypeptides or portions of polypeptides derivable from Salmonidae hatching fluid are present (in combination) at a range of 0.0001 to 10% w/w of the cosmetic composition (or up to 10-40%), e.g. 0.0001 to 5%, 0.0001 to 3%, 0.0001 to 2%, 0.0001 to 1%, 0.0001 to 0.5%, 0.0001 to 0.1% w/w of the cosmetic composition prepared according to the above method or are as described hereinafter, e.g. after dilution. Accordingly, individual polypeptides or portions of polypeptides derivable from Salmonidae hatching fluid may be present at the range of $1 \times 10^{-6}$ to 10% w/w of the cosmetic composition. In some embodiments said individual polypeptides or portions of polypeptides derivable from Salmonidae hatching fluid may be present at the range $1 \times 10^{-6}$ to 5% w/w of the cosmetic composition, e.g. $1 \times 10^{-6}$ to 4%, $1 \times 10^{-6}$ to 3%, $1 \times 10^{-6}$ to 2%, $1 \times 10^{-6}$ to 1%, $1 \times 10^{-6}$ to 0.5%, $1 \times 10^{-6}$ to 0.1% or $1 \times 10^{-6}$ to 0.01% w/w of the cosmetic composition.

The proportion of the polypeptides or portions of polypeptides derivable from Salmonidae hatching fluid in the cosmetic compositions may be defined relative to the other solutes in the composition, i.e. excluding solvents, e.g. water. Thus, said polypeptides or portions of polypeptides, in combination, may be present at the range of 1-100% w/w of the dry mass of the composition. In some embodiments the polypeptides or portions of polypeptides, in combination, may be present at the range of 1-90% w/w of the dry mass of the composition, e.g. 5-80%, 10-70%, 20-60%, 30-50% w/w of the dry mass of the composition. In other embodiments the polypeptides or portions of polypeptides, in combination, may be present at the range of 1-40%, 2-39%, 3-38%, 4-37% etc. w/w of the dry mass of the composition. Thus, individual polypeptides or portions of polypeptides may be present at the range of 0.0001 to 50% w/w of the dry mass of the composition, e.g. 0.0001 to 40%, 0.001 to 30%, 0.01 to 25% w/w of the dry mass of the composition. As described hereinafter the composition may be diluted for use according to the invention.

Whilst the invention is directed to methods for improving the cosmetic appearance of skin, this may include the treatment of a disorder, abnormality or condition, but in all cases the treatment is cosmetic in nature.

As referred to herein "cosmetic" is intended to refer to a treatment which does not cure, treat or prevent a disease or disorder, but instead serves as a skincare product or to modify or improve the appearance of the skin, e.g. the colour, texture or moisture content of the skin.

The basis of the treatments described herein is the skin anti-ageing effects of the cosmetic composition as disclosed herein. These effects have been shown in the Examples provided herein.

Thus treatments based on the anti-ageing properties of the cosmetic composition are contemplated.

The invention thus provides a cosmetic method of improving the appearance of skin of a mammalian animal, wherein a cosmetic composition as described hereinbefore is administered to said animal.

In a particularly preferred embodiment the skin is aged skin.

"Aged skin" refers to skin that displays one or more signs or symptoms of ageing, i.e. the appearance of wrinkles, fine lines, hyperpigmentation, laxity (sagging), dry skin, scaling or transepidermal water loss (TEWL). In particular, "aged skin" is determined relative to normal optimum skin, i.e. healthy, hydrated, normally pigmented and non-aged skin. In this respect, aged skin need not be related to the age of the subject and may be aged prematurely, e.g. by chronic exposure to sunlight (photo-damage). Thus, the relative parameters for "normal optimum skin" may be determined as the average measurements of the above signs of ageing from a number of subjects of the same or similar age to the subject in question, e.g. subjects that have not received chronic exposure to sunlight. Alternatively, the relative parameters for "normal optimum skin" may be taken as the measurements from subjects that are younger than the subject in question. In other words, the composition described herein may be used to restore the youthful appearance of skin, relative to the skin of the subject at an earlier age.

Thus, the invention provides a cosmetic method for the treatment of dermatoheliosis in a mammalian animal wherein a cosmetic composition as described hereinbefore is administered to said animal, preferably wherein said composition is administered topically.

Alternatively viewed, the invention provides a cosmetic composition as described hereinbefore for use in the treatment of dermatoheliosis in a mammalian animal, preferably wherein said cosmetic composition is for administration to the skin of said animal. In a particular embodiment the composition is for topical administration.

In a particularly preferred embodiment, improving the cosmetic appearance of skin (e.g. aged or photo-damaged skin) involves a reduction or prevention in the cosmetic appearance or prevalence of wrinkles, fine lines, hyperpigmentation, laxity, dry skin, scaling and/or transepidermal water loss. One or more of these parameters may be improved. Preferably fine lines and/or wrinkles are reduced.

Reduction or prevention in the cosmetic appearance or prevalence of the signs or symptoms of e.g. aged skin or dermatoheliosis, may mean that there is a reduction in the number and/or severity of the sign or symptom. For instance, the number of fine lines and wrinkles may be reduced and/or the size, e.g. the depth, of the wrinkles or fine lines may be reduced or minimized. Furthermore, reduction or prevention may involve stopping, or reducing the rate of, the appearance of new signs or symptoms.

"Dry skin" as referred to herein refers to an epidermis that lacks moisture or sebum, often characterized by a pattern of fine lines, scaling, and an itching and/or burning feeling. Dry skin can occur as a skin condition in itself (e.g. due to age) or may be the symptom of a skin disorder or condition such as sun-damage.

In this respect, the reduction of dry skin, scaling, fine-lines or transepidermal water loss may be achieved by the moisturizing effects of the composition described above.

Thus, the invention may be seen to provide a cosmetic method of moisturizing skin of a mammalian animal, wherein a cosmetic composition as defined herein is administered to said animal.

Alternatively stated, the present invention provides a cosmetic composition as described herein for use in moisturizing skin of a mammalian animal. (The composition may alternatively be used to prepare a cosmetic medicament for that purpose.)

"Moisturizing" as referred to herein covers moisturizers which prevent loss of water from the skin (e.g. TEWL) as well as moisturizers (humectants) that attract and retain water when applied to the skin and emollients (which improve defective desquamation).

As mentioned above, such moisturizing properties are advantageous for improving the cosmetic appearance of skin. In a particularly preferred embodiments, the skin is the skin of the face, ears, neck, hands or scalp.

"Wrinkles" are folds, ridges or creases in the skin. Skin wrinkles typically appear as a result of ageing processes. In this respect, the dermis comprises many of the structural elements of skin, which include collagen, which gives the skin its strength, glycosaminoglycans which give the skin its turgor, and elastin fibres which give the skin its elasticity or spring.

As the skin ages, the dermal layer gets thinner and the skin also produces less collagen. Moreover, the elastin fibres that provide elasticity wear out. These changes in the scaffolding of the skin cause the skin to wrinkle and sag. The rete-ridges of the dermal-epidermal junction flatten out, making the skin more fragile and making it easier for the skin to shear. This process also decreases the amount of nutrients available to the epidermis by decreasing the surface area in contact with the dermis, also interfering with the skin's normal repair process.

In the subcutaneous layer the fat cells get smaller with age. This leads to more noticeable wrinkles and sagging (laxity), as the fat cells cannot "fill in" the damage from the other layers.

Exposure to UVA and UVB radiation, i.e. sunlight, causes collagen to break down at a higher rate than with just chronologic ageing. Sunlight damages collagen fibres and causes the accumulation of abnormal elastin. When this sun-induced elastin accumulates, matrix metalloproteinases (MMP) are produced in large quantities. Normally, metalloproteinases remodel sun-injured skin by manufacturing and reforming collagen. However, this process does not always work well and some of the metalloproteinases actually break down collagen. This results in the formation of disorganized collagen fibres known as solar scars. The repetition of this imperfect rebuilding/regeneration process causes wrinkles to develop and skin laxity.

In a further preferred aspect, the skin condition to be treated or prevented cosmetically is a pigmentation condition, disorder or abnormality.

Pigmentation disorders or abnormalities of the skin, i.e. hyperpigmentation, may occur as a result of age or may result from premature ageing due to e.g. sun damage. Altered pigmentation may result from a local excess of melanocytes or increases in melanocyte activity, or both. Pigmentation disorders include liver, sun or age spots (solar lentigo) and other blemishes such as freckles.

As referred to herein "improving" the cosmetic appearance of skin is determined relative to normal optimum skin, i.e. healthy, hydrated, normally pigmented and non-aged skin. Hence, with respect to aged skin, one or more of the signs or symptoms of ageing may be measured as described in the Examples and compared to the same signs of skin that is chronologically or physiologically younger, preferably when an improvement is the reduction in one or more of the signs or symptoms of ageing.

In a preferred aspect the cosmetic uses are achieved by topical administration to the skin.

As used herein, "treating" refers to the reduction, alleviation or elimination, preferably to normal levels, of one or more of the cosmetic symptoms or effects of said condition or disorder e.g. presence or extent of dry skin, extent or area of pigmentation etc. relative to the symptoms or effects present on a different part of the body of said individual where the skin does not suffer from said condition or disorder and not subject to said treatment or in a corresponding normal individual not subject to said treatment.

"Preventing" or "reducing" refers to absolute prevention, or reduction or alleviation of the extent or timing (e.g. delaying) of the onset of that symptom or effect. For example conditions typified by dry, abnormally pigmented, wrinkled skin may be prevented by regular application of cosmetic compositions described herein before the appearance of such a condition.

The cosmetic methods of treatment or prevention according to the invention may advantageously be combined with administration of one or more active ingredients which are effective in treating or preventing the disorders or conditions and/or to achieve, e.g. moisturization. Thus, cosmetic compositions described herein may additionally contain one or more of such active ingredients.

According to a yet further aspect of the invention we provide compositions as herein defined and optionally one or more additional active ingredients as a combined preparation for simultaneous, separate or sequential use in human or mammalian animal therapy, as described herein.

The compositions described herein may be formulated in a conventional manner with one or more physiologically acceptable carriers, excipients and/or diluents, according to techniques well known in the art using readily available ingredients.

Thus, the compositions may be incorporated, optionally together with other active substances as a combined preparation, with one or more conventional carriers, diluents and/or excipients, to produce conventional galenic preparations such as powders, sachets, cachets, elixirs, suspensions (infusion fluids), emulsions, solutions, syrups, aerosols (as a solid or in a liquid medium), ointments, sterile packaged powders, and the like. The compositions may be stabilized by use of freeze-drying, undercooling or Permazyme.

Suitable excipients, carriers or diluents are lactose, dextrose, sucrose, sorbitol, mannitol, starches, gum acacia, calcium phosphate, calcium carbonate, calcium lactose, corn starch, aglinates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. Agents for obtaining sustained release formulations, such as carboxypolymethylene, carboxymethyl cellulose, cellulose acetate phthalate, or polyvinylacetate may also be used.

The compositions may additionally include lubricating agents, wetting agents, emulsifying agents, viscosity increasing agents, granulating agents, disintegrating agents, binding agents, osmotic active agents, suspending agents, preserving agents, sweetening agents, flavouring agents, adsorption enhancers (e.g. surface penetrating agents, e.g. bile salts, lecithins, surfactants, fatty acids, chelators), browning agents, organic solvent, antioxidant, stabilizing agents, emollients, silicone, alpha-hydroxy acid, demulcent, anti-foaming agent, moisturizing agent, vitamin, fragrance, ionic or non-ionic thickeners, surfactants, filler, ionic or non-ionic thickener, sequestrant, polymer, propellant, alkalinizing or acidifying agent, opacifier, colouring agents and fatty compounds and the like. Some of these components are described in more detail below.

Other active ingredients or components in the cosmetic composition may be selected from any one or more of minerals, vitamins, enzymes, proteins, peptides, amino acids, lipids, polysaccharides, substances suitable as sunscreen filters, chemical exfoliants, extracts, skin-conditioning agents, antioxidants and mixtures thereof.

Examples of proteins that may be combined with the composition of the invention include collagen and/or a derivative thereof (e.g. portions thereof as defined above), a protein or peptide which is capable of promoting cell growth, glycoprotein 1, glycoprotein 2 and laminin.

The composition of the invention may be combined with enzymes including, but not limited to, any one or more of, fruit enzymes (e.g. bromelain), superoxide dismutase, peroxidase, hyaluronidase and mucopolysaccharidase.

Peptides may be selected from, but are not limited to, any one or more of D,L-carnosine, D-carnosine, L-carnosine, anserine and Matrixyl (pentapetide derivative).

Amino acids may be selected from, but are not limited to, any one or more of L-alanine, L-arginine, L-asparagine, L-aspartic acid, L-cysteine, L-cystine, glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine, and L-valine and derivatives thereof including non-naturally occurring amino acids as defined in Table 1. Particularly preferred amino acids as antioxidants may be selected from any one or more of glycine, lysine, arginine, cysteine, cystine, histidine, tyrosine and tryptophan.

TABLE 1

| Non-conventional amino acid | Code | Non-conventional amino acid | Code |
| --- | --- | --- | --- |
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-αα-methylthreonine | Dmthr | N-cycloheptylglycine | Nchep |

TABLE 1-continued

| Non-conventional amino acid | Code | Non-conventional amino acid | Code |
|---|---|---|---|
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl)carbamylmethyl)glycine | Nnbhm | N-(N-(3,3-diphenylpropyl)carbamylmethyl)glycine | Nnbhe |
| 1-carboxy-1-(2,2-diphenyl-ethylamino)cyclopropane | Nmbc | L-O-methyl serine | Omser |
| | | L-O-methyl homoserine | Omhser |

The cosmetic composition may comprise one or more lipids which includes fats, oils, waxes and the like. Suitable polar oils are, for example, those from the group of lecithins and fatty acid triglycerides, namely the triglycerol esters of saturated and/or unsaturated, branched and/or unbranched alkanecarboxylic acids with a chain length of from 8 to 24, in particular 12 to 18, carbon atoms. The fatty acid triglycerides can, for example, be chosen advantageously from the group of synthetic, semisynthetic and natural oils, such as, for example, olive oil, sunflower oil, soya oil, peanut oil, rapeseed oil, almond oil, palm oil, coconut oil, castor oil, wheat germ oil, grape seed oil, thistle oil, evening primrose oil, macadamia nut oil and the like.

Alternatively or additionally the oil may be selected from volatile oils, non-volatile oils or mixtures thereof. Non-volatile oils include oils that fulfill at least one of the following definitions: (a) the oil exhibits a vapour pressure of no more than 0.2 mm Hg at 25° C. and one atmosphere pressure; (b) the oil has a boiling point at one atmosphere of at least 300° C. Volatile oils include materials that are not "non-volatile" as defined above.

Non-volatile oils may be selected from non-volatile silicone oils, non-volatile hydrocarbon oils and mixtures thereof. Suitable non-volatile silicone oils include linear polymethylsiloxanes and, preferably, non-volatile silicone oils are high molecular weight dimethicones. Examples of commercially available linear polymethylsiloxanes include Dow Corning Corporation 200® Fluid 20 Cst, Dow Corning Corporation 200® Fluid 100 Cst, Dow Corning Corporation 200® Fluid 350 Cst from Dow Corning Corporation.

Suitable non-volatile hydrocarbon oils include branched esters of diglycerin or triglycerin or the esters or 1, 2, 3, 4 butane triol or erythritol, di erythritol or tri erthyritol. Preferably, non-volatile hydrocarbon oils comprise erythrityl triethylhexanoate (available as Salacos® E-38 from Nisshin Oillio®) and Polyglyceryl-2 triisostearate (available as Cosmol® 43V from Nisshin Oillio®), diethyl hexyl carbonate (available as Tegosoft® DEC from Degussa®), dicapryl Ether (available as Cetiol® OE from Cognis® AG), dicapryl Carbonate (available as Cetiol® CC from Cognis® AG), isononyl isononanoate (available as Lanol™ 99 from Seppic®), tridecyl Neopentanoate (supplied as Ceraphyl® 55 from International Speciality Products), or a mixture thereof.

Volatile oils may be selected from volatile silicone oils, both functionalised and non-functionalised, volatile hydrocarbon oils and mixtures thereof. Volatile oil useful in the present invention may be saturated or unsaturated, have a straight or branched chain or a cyclic structure or have any one or more of these features.

Examples of volatile hydrocarbons oils include polydecanes such as isododecane and isodecane (e.g., Permethyl®-

99A which is available from Presperse® Inc.) and the C7-C15 isoparaffins (such as the Isopar™ Series available from Exxon Chemicals®).

The volatile silicone oil may be selected from cyclopentasiloxane, cyclohexasiloxane or a mixture thereof. Examples of commercially available volatile cyclic silicone oils include Dow Corning Corporation 244®, Dow Corning Corporation 245®, Dow Corning Corporation 344®, and Dow Corning Corporation 345® from Dow Corning Corp.; SF-1204™ and SF-1202™ Silicone Fluids from Momentive™ Performance Materials; GE 7207 and 7158 from General Electric Co.™); and, SWS®-03314 from SWS® Silicones Corp.

The linear volatile silicone oil may be a linear polymethylsiloxane. An example of commercially available linear polymethylsiloxanes include Dow Corning Corporation 200® Fluid, 5 Cst from Dow Corning Corp.

The cosmetic composition of the invention may further comprise one or more polysaccharides selected from, but not limited to, any one or more of anionic polysaccharides (e.g. alginic acid, pectin, xanthan gum, hyaluronic acid, chondroitin sulfate, gum arabic, gum karaya, gum tragacanth, carboxymethyl-chitin, cellulose gum, glycosaminoglycans), cationic polysaccharides (e.g. chitosan, acetylated chitosan, cationic guar gum, cationic hydroxyethylcellulose (HEC)), nonionic polysaccharides (e.g. starch, dextrins, guar gum, cellulose ethers such as hydroxyethylcellulose, methylcellulose and nitrocellulose), amphoteric polysaccharides (e.g. carboxymethylchitosan, N-hydroxy-dicarboxyethyl-chitosan, modified potato starch) and hydrophobic polysaccharides (e.g. cetyl hydroxyethylcellulose, polyquaternium24).

The cosmetic composition may further comprise a substance suitable as a sunscreen filter such as an organic sunscreen, e.g. a cinnamic derivative. The organic sunscreen active may be selected from hydrophilic organic sunscreen, hydrophobic organic sunscreen, or mixtures thereof. Suitable examples of sunscreens may be found in the CTFA International Cosmetic Ingredient Dictionary and Handbook, 7th edition volume 2, pp. 1672, edited by Wenning and Mc Ewen (The Cosmetic, Toiletry, and Fragrance Association, Inc., Washington, D.C. 1997).

The organic sunscreen may be selected from alkyl β,β-diphenylacrylate derivatives, α-cyano β,β-diphenylacrylate derivatives, anthranilate derivatives, benzophenone derivatives, camphor derivatives, dibenzoylmethane derivatives, p-aminobenzoic derivatives, salicylic derivatives, triazine derivatives, or mixtures thereof. For instance the hydrophobic organic sunscreen may be selected from 4-(1,1-dimethylethyl)-4'-methoxydibenzoylmethane; 4-isopropyldibenzoylmethane; 4-(1,1-di methylethyl)-4'-methoxydibenzoylmethane, 2-ethylhexyl-2-cyano-3,3-diphenylacrylate, or a mixture thereof.

An example of commercially available 4-(1, 1-dimethylethyl)-4'-methoxydibenzoylmethane, also known as butyl methoxydibenzoylmethane or Avobenzone®, includes Parsol™ 1789 from Givaudan Roure S. A. and Eusolex™9020 from Merck & Co., Inc. An example of commercially available 4-isoproplydibenzoylmethane, also known as isopropyldibenzoylmethane, includes Eusolex™ 8020 from Merck & Co., Inc. Examples of commercially available 2-ethylhexyl-2-cyano-3,3-diphenylacrylate, also known as Octocrylene®, include Uvinul® N539 SG from BASF; and Eusolex™ OCR from Rona/Merck.

In some embodiments the hydrophilic organic sunscreen may be 2-phenylbenzimidaole-5-sulfonic acid. An example of commercially available 2-phenylbenzimidaole-5-sulfonic acid, also known as PBSA, includes Eusolex™ 232 from Rona/Merck.

Suitable examples of cinnamic derivative sunscreens may be found in the CTFA International Cosmetic Ingredient Dictionary and Handbook, 7th edition volume 2, pp. 1672, edited by Wenning and Mc Ewen (The Cosmetic, Toiletry, and Fragrance Association, Inc., Washington, D.C. 1997). The cinnamic derivative may be selected from 2-ethylhexyl-p-methoxycinnamate, diethanolamine methoxycinnamate, 2-ethoxyethyl-p-methoxycinnamate, or a mixture thereof. For instance, the cinnamic derivative may be 2-ethylhexyl-p-methoxycinnamate.

The cosmetic composition may be combined with a chemical exfoliant selected from, but not limited to, any one more of alpha hydroxy acids (AHAs), beta hydroxy acids (BHAs) or poly-hydroxy acids, such as salicylic acid, glycolic acid, citric acid and malic acid.

Extracts that may be incorporated in the cosmetic composition include, but are not limited to plant extracts, which may comprise phenolic compounds such as, for example, flavonoids (e.g., glycosyl rutin, ferulic acid, caffeic acid), furfurylidene glucitol, butylated hydroxytoluene, butylated hydroxyanisole, nordihydroguaiaretic resin acid, nordi-hydroguaiaretic acid, trihydroxybutyrophenone and derivatives thereof. Particular plant extracts for use in the composition of the invention include aloe vera extract, ginseng extract and horsetail extract.

Ginseng extract is obtainable by extracting with a hydrophilic solvent (in particular, water, ethanol, glycol, or any mixtures thereof) the root of *Panax ginseng*. The extract contains saponins, sterols, carbohydrates, pectin, vitamins, minerals and lipids.

Horsetail extract is obtainable by extracting with a hydrophilic solvent (e.g., water, ethanol, glycol, or any mixtures thereof) the whole herb of *Equisetum arvense*. The extract contains silicates, flavinoids, saponosides, caffeic acid and ferulic acid.

The cosmetic composition may further comprise a skin-conditioning agent. The skin-conditioning agent may be selected from humectants, exfoliants, emollients or mixtures thereof. Humectants includes polyhydric alcohols such as glycerine, propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerine or mixtures thereof.

Examples of antioxidants that may be combined with the composition of the invention include but are not limited to amino acids, vitamins, minerals, carotenoids, peptides, thiols, sulfoximine compounds, chelators, unsaturated fatty acids, phenolic compounds, plant extracts, stilbenes, uric acid, mannose, chlorogenic acid, imidazoles (e.g. urocanic acid), furfurylidenesorbitol, ubiquinone, ubiquinol, plastoquinone, phytosterols and derivatives thereof (e.g. salts, esters, ethers, sugars, nucleotides, nucleosides, peptides and/or lipid derivatives), some of which are described above.

Vitamins may be selected from, but are not limited to, any one or more of vitamin A and derivatives thereof (e.g. retinoid or retinol or their derivatives such as retinyl palmitate or retinyl proprionate), biotin, folic acid, calcium pantothenate, nicotinamide, pyridoxine HCl, pyridoxal HCl, riboflavin, thiamine HCl, thymidine, vitamin B12, vitamin B3 (e.g. niacinamide), vitamin B5 (e.g. panthenol), vitamin C and derivatives thereof (e.g., ascorbyl palmitate, Mg ascorbyl phosphate, ascorbyl acetate), tocopherols and derivatives (e.g. vitamin E acetate).

Minerals may be selected from, but are not limited to, any one or more salts of molybdenate (e.g. $(NH_4)OMo_7O_{24}$) aluminium (e.g. $AlCl_3$), calcium (e.g. $CaCl_2$), cobalt (e.g. $CoCl_2$), chromium (e.g. $CrK(SO_4)$), copper (e.g. $CuSO_4$), iron (e.g. $Fe(NO_3)_3$, $FeSO_4$), potassium (e.g. KCl), magnesium (e.g. $MgCl_2$), manganese (e.g. $MnCl_2$, $MnSO_4$), phosphate (e.g. $Na_2HPO_4$, $NaH_2PO_4$), carbonate (e.g. $NaHCO_3$), silicate (e.g. $Na_2SiO_3$), sodium (e.g. NaCl), vanadate (e.g. $NH_4VO_3$), nickel (e.g. $NiCl_2$), tin (e.g. $SnCl_2$), zinc (e.g., ZnO, $ZnSO_4$), selenium (e.g. selenomethionine, ebselen, $H_2SeO_3$, $Na_2SeO_3$), sulphate and nitrate.

Carotenoids, may be selected from, but are not limited to, any one or more of carotenes, e.g. α-carotene, β-carotene, ψ-lycopene, phytoene etc. and derivatives thereof.

Thiols may be selected from, but are not limited to, any one or more of aurothioglucose, propylthiouracil, thioredoxin, lipoic acid, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters and the salts thereof, dilauryl thiodipropionate, distearyl thiodipropionate, thiodipropionic acid and derivatives thereof.

Sulfoximine compounds may be selected from, but are not limited to, any one or more of homocysteine sulfoximine, buthionine sulfones, penta-, hexa-, heptathionine sulfoximine, which may be included in the composition such that they are provided in very low dosages (e.g. pmol to µmol/kg).

Chelators may be selected from, but are not limited to, any one or more of apoferritin, desferral, lactoferrin, α-hydroxy fatty acids, palmitic acid, phytic acid, α-hydroxy acids (e.g. citric acid, lactic acid, malic acid), humic acid, bile acid, bile extracts, bilirubin, biliverdin, EDTA, EGTA and derivatives thereof.

Unsaturated fatty acids may be selected from, but are not limited to, any one or more of γ-linolenic acid, linoleic acid, oleic acid and derivatives thereof.

Stilbenes and derivatives thereof include, for example, stilbene oxide and trans-stilbene oxide.

A variety of additional optional active ingredients may be incorporated into the cosmetic compositions of the present invention. Non-limiting examples of these additional ingredients include additional skin care actives such as farnesol, bisabolol, phytantriol, urea, guanidine (e.g. amino guanidine); hexaminidine compounds, salts or derivatives thereof; sugar amines; self-tanning agents (e.g. dehydroxyacetone); structuring agents; hydrophilic gelling agents; anti-acne medicaments (resorcinol, salicylic acid, and the like); skin soothing and healing agents such as allantoin and the like; and agents suitable for aesthetic purposes such as essential oils, fragrances, skin sensates, opacifiers, aromatic compounds (e.g. clove oil, menthol, camphor, eucalyptus oil, and eugenol). The compositions described herein may be formulated so as to provide quick, sustained or delayed release of the active ingredients after administration to the body by employing techniques well known in the art.

The composition may be in any appropriate dosage form to allow delivery or for targeting particular cells or tissues, e.g. as an emulsion or in liposomes, niosomes, microspheres, nanoparticles or the like with which the active ingredient may be absorbed, adsorbed, incorporated or bound. This can effectively convert the product to an insoluble form. These particulate forms may overcome both stability (e.g. degradation) and delivery problems.

The use of solutions, suspensions, gels and emulsions are preferred, e.g. the active ingredient may be carried in water, a gas, a water-based liquid, an oil, a gel, an emulsion, an oil-in water or water-in-oil emulsion, a dispersion or a mixture thereof.

The emulsifier may be selected from nonionic emulsifiers, anionic emulsifiers, cationic emulsifiers, zwitterionic emulsifiers, amphoteric emulsifiers or mixtures thereof. Emulsifiers are known in the art. See, e.g., McCutcheon's, Detergents and Emulsifiers, North American Edition (1986), published by Allured Publishing Corporation.

When the cosmetically acceptable carrier is a water-in-silicone emulsion, emulsifiers are preferably selected from polyoxyalkylene copolymers, polyglyceryl copolymers or mixtures thereof. Polyoxyalkylene copolymers, also known as silicone polyethers, are described in detail in U.S. Pat. No. 4,268,499. An example of commercially available polyoxyalkylene copolymers includes Dow Corning Corporation 5225C® or Dow Corning Corporation 2-5185C® (PEG/PPG-18/18 dimethicone available as blend with cyclopentasiloxane) from Dow Corning Corp.; and, KF6017™ or KF6028™ (PEG-9 dimethicone) from Shin-Etsu Inc. Examples of commercially available polyglyceryl emulsifiers include KF6100™ and KF6104™ from Shin-Etsu Inc.

Compositions are preferably for topical (i.e. to the skin) administration.

Topical compositions include gels, creams, ointments, sprays, lotions, salves, sticks, soaps, powders, films, aerosols, drops, foams, solutions, emulsions, suspensions, dispersions e.g. non-ionic vesicle dispersions, milks and any other conventional cosmetic forms in the art.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant.

In some embodiments the cosmetic compositions described herein may be topically administered to the skin via a product, device or material to which the polypeptide or composition has been applied, impregnated or chemically bonded. To this end, bandages, plasters (e.g. adhesive patches), gauze, surgical tape, cotton swabs or other absorbent materials, e.g. a puff, fleece, or sponge, or supportive matrices may be coated, impregnated or chemically bonded with a composition as described herein. For example, many compositions can be applied to the skin using dermal patches that are well described in the art, e.g. US 2008/0038300, US 2009/0043236, WO 2005/067499 and WO 2009/085302, which are incorporated herein by reference. In some embodiments, the material comprising the composition as described herein may be in the form of a device that can be, e.g. worn by the subject to be treated. For instance, the composition as described herein may be applied, impregnated or chemically bonded onto a material or supportive matrix that forms all or part of a diaper, glove, sock etc.

The cosmetic compositions can be included in a container, pack, or dispenser together with instructions for administration.

Hence, a further aspect of the invention comprises the provision of a product, material or device which is coated, impregnated or chemically bonded with a composition as described herein. The invention also extends to such products, materials or devices for uses as described herein. Preferably said product is a bandage, plaster (e.g. adhesive patch), gauze, surgical tape or cotton swab or said device is a diaper, glove or sock.

The concentration of the active ingredients in compositions described herein, may depend upon the source of the composition (i.e. the starting material for the method described above), the mode of administration, the course of treatment, the age and weight of the patient, the cosmetic indication, the body or body area to be treated and may be varied or adjusted according to choice. Generally however, concentration ranges for the composition described herein is 0.001, 0.005, 0.01 or 0.1 to 50%, e.g. 0.005-40%, e.g. 0.1 to 25%, such as 0.1 or 0.5 to 5, e.g. 1-5% (w/w or v/v of the final preparation for administration, particularly for topical administration) e.g. a 1% solution of the aforementioned composition prepared according to the method of the invention.

When additional components are added to the composition made by the above described method, e.g. additional moisturizing agents as described herein, the additional component may be present in the amounts 0.0001, 0.0005, 0.001 or 0.01 to 50%, e.g. 0.0005-40%, e.g. 0.01 to 25%, such as 0.1 or 0.5 to 5, e.g. 1-5% (w/w of the final preparation for administration, particularly for topical administration). Effective single doses for the composition may lie in the range of from 0.0001-100 mg/cm$^2$/day (total protein in the composition), e.g. 0.1-100 mg/cm$^2$/day, preferably 0.0001-10 mg/cm$^2$/day, e.g. 0.1-10 mg/cm$^2$/day, when applied topically, depending on the mammalian animal being treated, taken as a single dose.

Preferably liquid solutions, creams or suspensions would be employed for topical administration.

Animals to which the compositions may be applied or administered are limited to mammals. Preferably the mammals are primates, domestic animals, livestock and laboratory animals. Thus preferred mammalian animals include mice, rats, rabbits, guinea pigs, cats, dogs, monkeys, pigs, cows, goats, sheep and horses. Especially preferably the compositions are applied, or administered, to humans.

The following Examples are given by way of illustration only in which the Figures referred to are as follows:

FIG. 1 shows a photograph of a subject treated with the hatching fluid composition of the invention before treatment (Baseline), after 2 weeks and after 12 weeks of treatment. The reduction in various signs of aged skin are evident after both 2 and 12 weeks. The values provided indicate the average changes for 35 participants.

EXAMPLE 1: PREPARATION OF THE COMPOSITION

Figure 1:
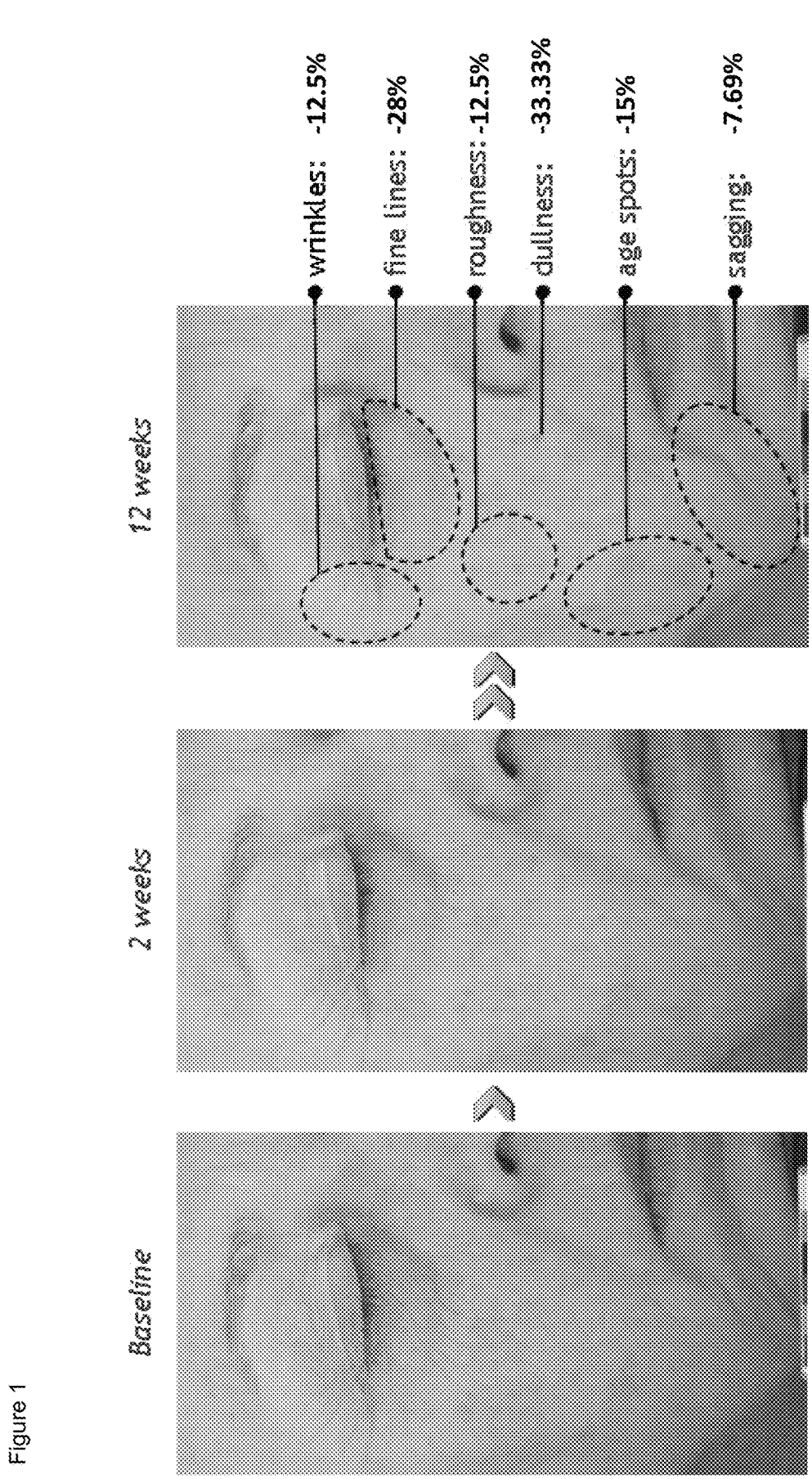

The composition was prepared from salmon hatching fluid. To improve the protein concentration of hatching fluid, salmon eggs were transferred to minimal volumes of water prior to hatching. Highly synchronous hatching can be induced by elevated (room) temperatures, or by deoxygenation (Oppen-Berntsen et al. 1990, Aquaculture, 86, pp. 417-430), which yields a small volume of highly concentrated preparation of crude polypeptides and portions of polypeptides. Hatching should be complete within 2 hours for more than 95% of the embryos.

The hatching fluid was filtered using a standard filter with a 7 μm pore size, to remove material likely to clog filters in subsequent filtration steps. This filtrate, the processed hatching fluid, may be frozen for years without significant degradation, before being thawed and employed for further protein purification. This fact greatly simplifies production of a starting material for purifying the hatching fluid composition.

The processed hatching fluid was subjected to filtration using a filter with a 0.45 μm pore size and the filtrate was collected. The filtrate was then dia-filtrated with a filter exclusion size of 8 kDa to exchange water of hatching fluid for buffer. In this case, the buffer contained 0.5 mM phosphate and 1 mM NaCl, although other buffers are equally suitable. For example, phosphate buffered saline or buffers containing millimolar Tris (e.g. 10 mM) at pH around neutrality or slightly alkaline (pH 7.5-8.5), containing 5 mM NaCl, are suitable. The retentate from the diafiltration step was collected and diluted by the addition of the buffer so that the enzymatic activity of the filtrate, as defined above, was equal to 3400 mU/litre.

Finally, the filtrate was subjected to filtration through a filter with a pore size of 0.22 μm and the final filtrate was collected. This filtrate is an enriched preparation of the polypeptides and portions of polypeptides, found in the crude hatching fluid.

EXAMPLE 2: IN VIVO EFFECTS OF HATCHING FLUID COMPOSITION ON AGED SKIN

The hatching fluid composition was prepared as described in Example 1. The composition was prepared as a 1% and 3% skin lotion [v/v] (total volume of composition per unit volume of lotion), the two active skin lotions in the trial, and compared to a control skin lotion which did not comprise the active component, i.e. the hatching fluid composition. The skin lotion was an oil in water (O/W) emulsion. The oil phase represents 9% of the total composition and was emulsified with hydrogenated lecithin.

A double blind, placebo controlled clinical trial was conducted to evaluate the effectiveness and tolerance of topical skin treatments in females with mild to moderate photodamaged, i.e. aged, facial skin. The duration of this trial was 12 weeks with visits at baseline, Week 2, Week 6 and Week 12. Efficacy was assessed using visual grading, instrumentation, digital VISIA CR photographs and subject self-assessment questionnaires.

Number of Subjects

One hundred and one (101) female subjects completed participation in the study (N>30 for the three treatments, i.e. one placebo and two compositions comprising the hatching fluid component at different concentrations).

Subject Population and Identification

Subjects were healthy females ages 40 to 65 and were assigned a three-digit number which, when used in conjunction with the clinical study number, uniquely identified every subject in the study. This number remained with the subject throughout the study to maintain the anonymity of the experiment.

Eligibility Criteria

Inclusion Criteria

1. Females, ages 40 to 65, inclusive, who were in general good health as determined by the health and eligibility questionnaire.

2. Willingness to cooperate and participate by following study requirements for the duration of the study and to report any adverse symptoms immediately 3. Clinically determined mild to moderate photodamage (fine lines, wrinkles, hyperpigmentation, laxity and roughness) on the face corresponding to the modified Griffith's grading scale with scores of 3-7.

4. Free of any disease state or physical facial skin conditions (e.g. atopic dermatitis, eczema, psoriasis, seborrheic dermatitis) which might impair evaluations of the test sites or increase the health risk to the subject by study participation.

5. Willingness to avoid extended periods of sun exposure and all use of tanning beds for the duration of the study. Extra care should be taken to wear protective clothing, including sunglasses, and avoid sun exposure from 10 AM to 4 PM.

6. Willingness to continue use of all regular brands of colour cosmetics, cleanser, toner (if applicable) and makeup remover for the duration of the study. Individuals had to refrain from using any anti-ageing products or skin lightening products other than the assigned test material.

7. Willingness to remove all makeup at least 20 minutes prior to each scheduled clinic visit. No other topical products were to be applied to the face or eye area until the study visit was completed. If a subject arrived having not removed all makeup, she was required to remove the residual makeup at the clinic and wait at least 20 minutes prior to procedures.

8. Individuals who were taking hormone replacement therapies or hormones for birth control had to be on a stable regimen for at least one month prior to the study start and they had to be willing to continue and not change this medication for the duration of the study. Individuals who were not taking HRT or hormones at the start of the study had to be willing to not begin use during the course of the study.

9. Willingness to cooperate and participate by following study requirements and to report any adverse symptoms immediately.

Exclusion Criteria

1. Individuals with a history of intolerance or allergy to any personal care product.

2. Individuals who had used any prescription or OTC skin lightening products less than 30 days prior to the study entry.

3. Individuals who had a condition and/or disease of the skin that the examining Investigator deemed inappropriate for participation.

4. Individuals who were nursing, pregnant, or planning to become pregnant during the study.

5. Individuals who had routinely used any anti-ageing, anti-wrinkle, topical antioxidants, less than 30 days prior to the study entry.

6. Individuals who had used an enzymatic facial skin treatment within 6 months of the study start.

7. Use of Retin-A®, Retin-A Micro®, Renova®, Avita®, Tazorac®, Avage® or Differin® or other topical retinoids within 3 months of the study start, or had taken Accutane or an oral retinoid within the past 6 months.

8. Routine use of products containing alpha-, beta- or poly-hydroxyacid (including salicylic acid and Lachydrin), retinol or derivatives of retinol or other 'anti-ageing' products on the face within 30 days of the study start.

9. Individuals who had received a facial dermabrasion or chemical peel treatment within 3 months of treatment or during the study.

10. Individuals who had received treatment with light RF, or other devices in the treated area within the treated area within 6 months of treatment or during the study.

11. Individuals who had received Botox, collagen, fat injections or other methods of augmentation with injected or implanted material in the treated area within 9 months of treatment or during the study.

12. Individuals who had undergone a resurfacing procedure, face lift or eye or eyelid surgery within 12 months prior to the start of this trial.

13. Individuals who had pre-existing and/or dormant dermatologic conditions on the face (e.g., vitiligo, atopic dermatitis, psoriasis, rosacea, eczema, seborrheic dermatitis, severe excoriations etc.) or medical condition/disease which in the opinion of the Investigator could have interfered with the outcome of the study.

14. Individuals who had a history of immunosuppressant/immune deficiency disorders (including (HIV infection or AIDS) or currently using immunosuppressive medications.

15. Individuals who were participating in any other clinical usage study (patch studies are acceptable).

16. Individuals who had an uncontrolled disease such as diabetes, hypertension, hyperthyroidism or hypothyroidism. Some individuals who had multiple health conditions were excluded from participation even if the conditions are controlled by diet, medication, etc.

17. Individuals who had participated in any clinical trial within 28 days prior to inclusion into the study.

Individuals were admitted to the study at the discretion of the Investigator or his designate based on medical history and findings of the pre-study interview and examination.

Study Design

The double blind, placebo controlled clinical trial was conducted to evaluate the effectiveness of topical skin treatments in females with mild to moderate photodamaged, i.e. aged, facial skin. The duration of this trial was 12 weeks with visits scheduled at baseline, Week 2, Week 6 and Week 12. Efficacy was assessed using visual grading, instrumentation, digital VISIA CR photographs and subject self-assessment questionnaires.

Three groups of N>30 per group completed the study. Subjects received an active skin treatment, namely the hatching fluid composition described above, or a vehicle control (water) to apply to the face for twelve weeks. Randomization of subjects into the 3 groups was performed according to a pre-determined randomization.

|  | Visit: | | | |
|---|---|---|---|---|
|  | Visit 1 Baseline | Visit 2 Week 2 | Visit 2 Week 6 | Visit 2 Week 12 |
| Informed Consent, eligibility paperwork, facial screening | X | | | |
| Right and left side clinical scoring for lines, wrinkles, mottled hyperpigmentation, laxity, clarity and roughness | X | X | X | X |
| Right and left side clinical scoring for objective and subjective irritation (erythema, dryness, burning/ stinging*, itching*, tight/ dry feeling*) *reported by the panelist. | X | X | X | X |
| Right and left side VISIA-CR imaging | X | X | X | X |
| Cutometer measurements on the right and left face. | X | X | X | X |
| Transepidermal water loss (TEWL) measurements on the right and left face. | X | X | X | X |
| Distribution of test material, vehicle, usage instructions, diary and calendar | X | | X | |
| Completion of self assessment questionnaires for right and left face. | | X | X | X |
| Diary review and product weighing for compliance | | X | X | X |

Efficacy and Tolerability Evaluations

An expert clinical grader assessed the right and left side of the face for the parameters shown below. A modified Griffith's scale was used, where 0=none, 1-3=mild, 4-6=moderate and 7-9=severe. Half points were used when needed to better describe the skin condition.

Fine Lines
Wrinkles
Hyperpigmentation
Laxity
Dull/Matte (Clarity)
Tactile Roughness An expert clinical grader assessed the right and left side of the face for the parameters shown below. A four point scale was used, where 0=none, 2=mild, 3=moderate and 4=severe. Half points were used when needed to better describe the skin condition.

Erythema
Dryness/scaling
Burning/stinging feeling
Itching
Tight/dry feeling
Digital VIS/A CR Photography VISIA-CR imaging was taken of the right and left sides of the face. The subjects were imaged such that their hair was pulled back, jewellery was removed, eyes were closed, the subject was centered within the frame and had a neutral facial expression.

Transepidermal Water Loss (TEWL)

Prior to Instrumental measurements, subjects were made to equilibrate to ambient conditions of the clinic for at least 20 minutes. Ambient conditions were recorded hourly during the study visits. During this time, subjects were graded, completed questionnaires and/or had VISIA CR imaging performed.

The Tewameter was used to take a transepidermal water loss (TEWL) measurement at all visits. Measurements were taken on the right and left cheek at the intersection of lines extending down from the corner of the eye and horizontally across the bottom of the nose.

The Tewameter measures TEWL utilizing an open chamber system. A hand held probe placed on the skin surface sampled relative humidity at two points above the surface, allowing the rate of water loss to be calculated from the measured humidity gradient.

Cutometer MPA 580

All subjects had Cutometer measurements taken at all visits. The Cutometer was used to assess the viscoelastic properties (i.e. extensibility and elasticity) of the skin. The instrument applies a vacuum to a small area of skin and measures the elastic response of the skin (movement of the skin into and out of the aperture) by an optical technique.

For this study, the 2 mm probe was used, a vacuum of 300 mbar was applied and two cycles of suction and release were performed. Cycle times was 5 seconds on and 10 seconds off.

Measurements were taken on the right and left cheek at the intersection of lines extending down from the corner of the eye and horizontally across the bottom of the nose, or an alternate location near the jaw.

Skin Assessment and Self-Assessment Questionnaires

Subjects completed a skin self assessment questionnaire containing questions that describe how the subject perceives their facial skin appearance and condition on the right and left sides of the face.

Results

Fine Lines

Figure 2:
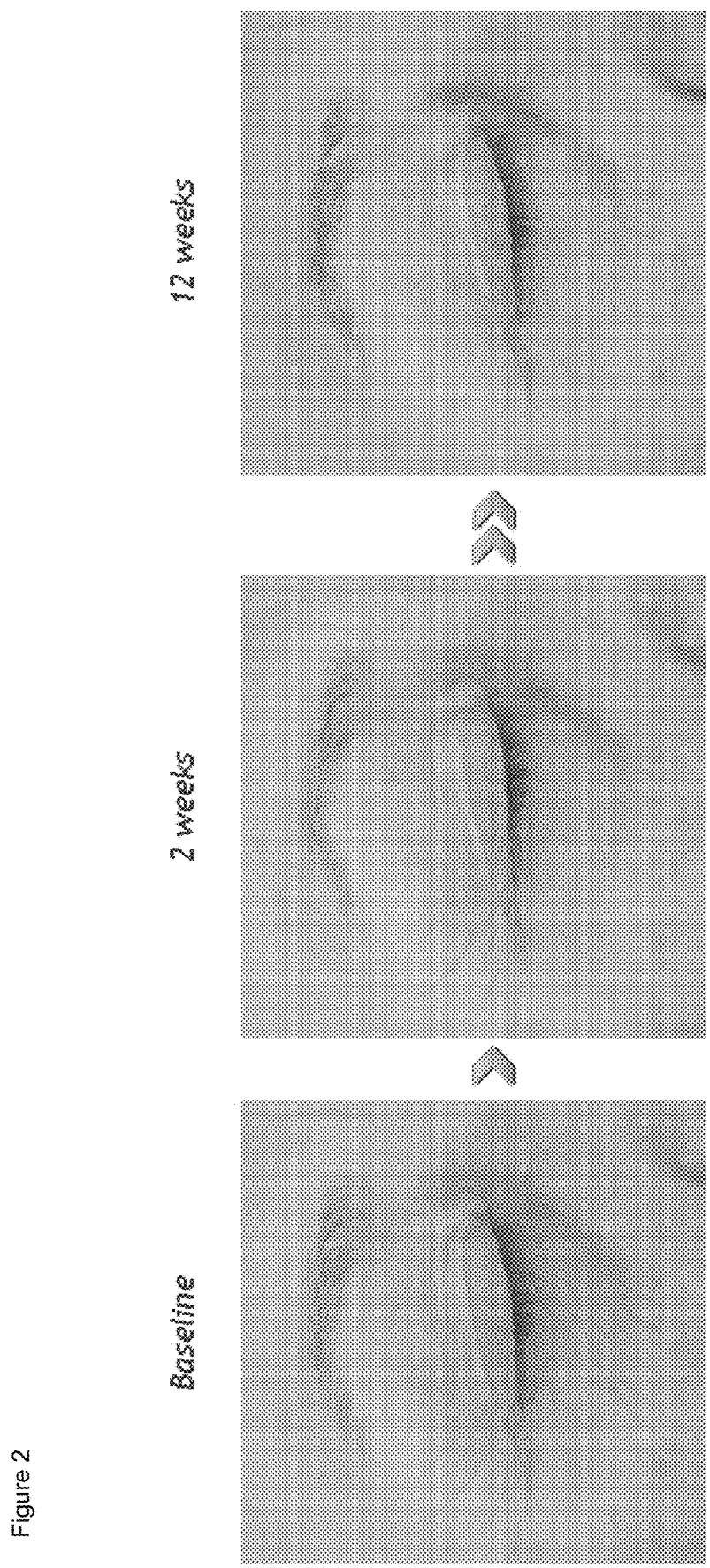
FIG. 2 shows a close-up photograph of the subject in FIG. 1 to emphasise the reduction of fine lines and wrinkles seen after 2 and 12 weeks of treatment with the hatching fluid composition of the invention.

At week 2 subjects treated with a skin lotion comprising one of the active compositions showed a reduction in fine lines (e.g. percentage change of 5.59% (1% solution) and 5.65% (3% solution)) in comparison to the placebo (4.58%). The reduction in fine lines continued at week 6 (e.g. 14.34% (1% solution), 14.86% (3% solution) and 8.98% (placebo)) and week 12 (e.g. 23.43% (1% solution), 25.99% (3% solution) and 14.68% (placebo)). FIGS. 1 and 2 show a subject with a 28% reduction of fine lines.

Wrinkles

Figure 3:
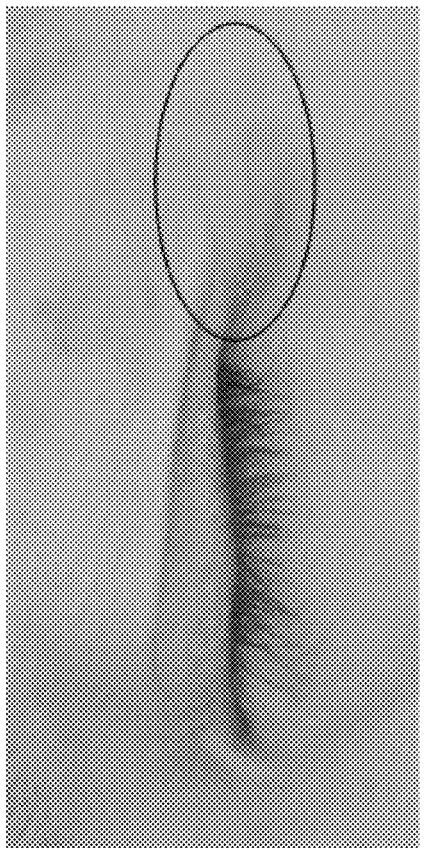
FIG. 3 shows a close-up photograph of a subject treated with the hatching fluid composition of the invention before treatment (Baseline) and after 12 weeks of treatment. The circled area shows a clear reduction of wrinkles after 12 weeks of treatment.
Figure 3:
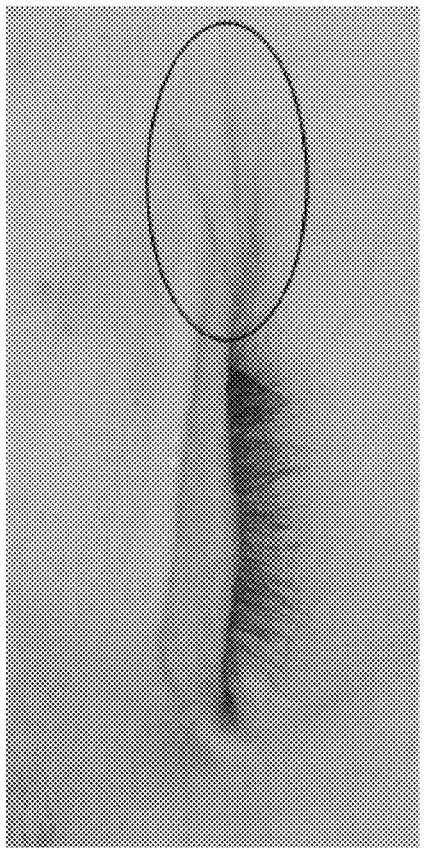

At week 2 subjects treated with a skin lotion comprising one of the active compositions showed a reduction in wrinkles (e.g. percentage change of 2.15% (1% solution) and 1.75% (3% solution)) in comparison to the placebo (0.70%). The reduction in wrinkles continued at week 6 (e.g. 6.13% (1% solution), 7.32% (3% solution) and 3.70% (placebo)) and week 12 (e.g. 14.72% (1% solution), 15.15% (3% solution) and 9.57% (placebo)). FIG. 1 shows a subject with a 12.5% reduction in wrinkles. FIG. 3 shows a subject with a 26.32% reduction in wrinkles.

Hyperpigmentation

At week 2 subjects treated with a skin lotion comprising one of the active compositions showed a reduction in hyperpigmentation (e.g. percentage change of 2.11% (1% solution) and 2.68% (3% solution)) in comparison to the placebo (0.40%). The reduction in hyperpigmentation continued at week 6 (e.g. 5.61% (1% solution), 7.91% (3% solution) and 3.16% (placebo)) and week 12 (e.g. 10.53% (1% solution), 15.35% (3% solution) and 5.73% (placebo)). FIG. 1 shows a subject with an 15% reduction in the pigmentation of an age spot after 12 weeks.

Laxity

At week 2 subjects treated with a skin lotion comprising one of the active compositions showed a reduction in laxity (e.g. percentage change of 2.64% (1% solution) and 1.62% (3% solution)) in comparison to the placebo (0.87%). The reduction in laxity continued at week 6 (e.g. 6.33% (1% solution) and 6.61% (3% solution), 2.51% (placebo)) and week 12 (e.g. 10.55% (1% solution) and 11.33% (3% solution), 5.18% (placebo)). FIG. 1 shows a subject with a 7.69% reduction in laxity (sagging) after 12 weeks.

Dull/Matte (Clarity)

At week 2 subjects treated with a skin lotion comprising one of the active compositions showed an improvement in skin clarity (e.g. percentage change of 12.95% (1% solution) and 16.00% (3% solution)) in comparison to the placebo (10.67%). The improvement continued at week 6 (e.g. 29.26% (1% solution), 28.50% (3% solution) and 19.07% (placebo)) and week 12 (e.g. 37.17% (1% solution), 39.18% (3% solution) and 26.72% (placebo)). FIG. 1 shows a subject with a 33.33% reduction in dullness.

Tactile Roughness

At week 2 subjects treated with a skin lotion comprising one of the active compositions showed a reduction in the tactile roughness of the skin (e.g. percentage change of 16.51% (1% solution) and 20.24% (3% solution)) in comparison to the placebo (13.38%). The improvement continued at week 6 (e.g. 24.77% (1% solution), 26.65% (3% solution) and 16.79% (placebo)), but there was not a further reduction at week 12 (e.g. 26.61% (1% solution), 29.19% (3% solution), and 15.79% (placebo)). FIG. 1 shows a subject with a 12.5% reduction in tactile roughness.

Dryness/Scaling

At week 2 subjects treated with a skin lotion comprising one of the active compositions showed a reduction in the dryness/scaling of the skin (e.g. percentage change of 72.09% (1% solution) and 100.00% (3% solution)) in comparison to the placebo (64.71%). However, at week 6 (e.g. 86.05% (1% solution), 84.62% (3% solution) and 100.00% (placebo)), and week 12 there was not a further reduction when compared to the placebo (e.g. 90.70% (1% solution), 100.00% (3% solution) and 89.47% (placebo)).

TEWL

Whilst subjects treated with a skin lotion comprising one of the active compositions showed a reduction in TEWL at week 2, this was not clearly different to the placebo (e.g. percentage change of 15.35% (1% solution) and 14.53% (3% solution)) in comparison to the placebo (17.26%). However, at week 6 (e.g. 29.46% (1% solution), 26.66% (3% solution) and 22.96% (placebo)), and week 12 there was a further reduction greater than that of the placebo (e.g. 37.46% (1% solution), 40.04% (3% solution), and 34.21% (placebo)).

Extensibility

Whilst subjects treated with a skin lotion comprising one of the active compositions showed an improvement in the extensibility of the skin at week 2, this was only slightly different to the placebo (e.g. percentage change of 16.18% (1% solution) and 17.21% (3% solution)) in comparison to the placebo (10.82%). At week 6 there was no clear difference between the three treatments (e.g. 18.04% (1% solution), 17.18% (3% solution) and 19.90% (placebo)), but at week 12 there was a further improvement for the skin treatment with the compositions comprising the active component, which was greater than that of the placebo (e.g. 31.84% (1% solution), 33.57% (3% solution), and 16.48% (placebo)).

Figure 4:
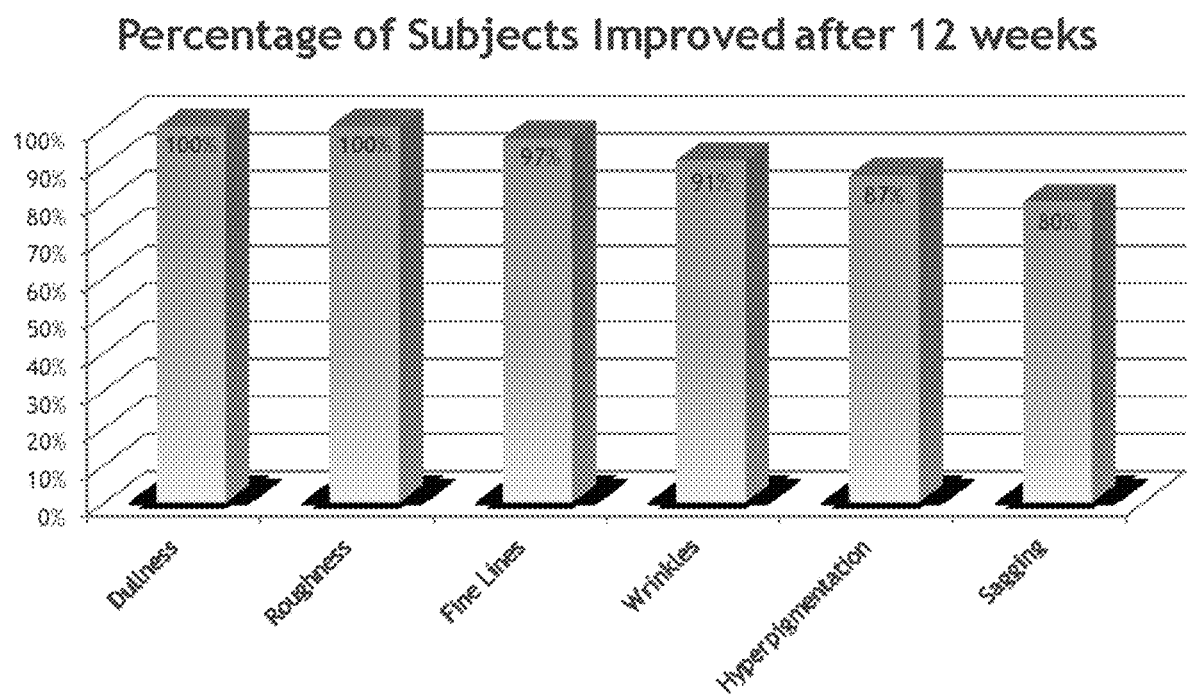
FIG. 4 shows a bar chart depicting the percentage of subjects that were considered to have improved in various signs of ageing based on a tactile/visual clinical grading on both sides of the face.

A comparison of the tactile/visual clinical grading on both sides of the face performed at the start of the study (baseline) and after 12 weeks of treatment shows that the all of the subjects showed improvements in the dullness and roughness of their skin following treatment with the hatching fluid composition of the invention and the majority of subject showed improvements in fine lines (97% of subjects), wrinkles (91% of subjects), hyperpigmentation (87% of subjects) and sagging (80% of subjects) (FIG. 4).

Questionnaires reveal that from 6 weeks of use statistically significant differences were found for mean scores of statements about overall appearance, overall feel, smoothness, softness, clarity and elasticity between the placebo and the cosmetic composition comprising the hatching fluid composition of the invention.

Thus, it is evident from the above results that the hatching fluid extract composition demonstrated an effect on each aspect of aged skin in comparison to the placebo.

EXAMPLE 3: COMPARATIVE IN VITRO STUDY OF EFFECTS OF HATCHING FLUID COMPOSITION ON RECONSTRUCTED HUMAN EPIDERMIS RELATIVE TO KNOWN COSMETIC SKIN TREATMENTS

In vitro reconstructed human epidermis consists of normal human keratinocytes cultured on an inert polycarbonate filter at the air-liquid interface, in a chemically defined medium. This in vitro model is histologically similar to that of the in vivo human epidermis.

Reconstructed Human Epidermis (SkinEthic®) was exposed on the stratum corneum side for 12 hours, 24 hours or 48 hours to 200 µl of one of the following solutions:

1% Hatching fluid composition;
5% Glycolic Acid (AHA);
1 mU/ml Bromelain (fruit enzyme); or
$dH_2O$ (control).

After exposure the cultures were fixed in 4% (w/v) paraformaldehyde in PBS at 4° C. and analysed by scanning electron or light microscopy.

Figure 5:
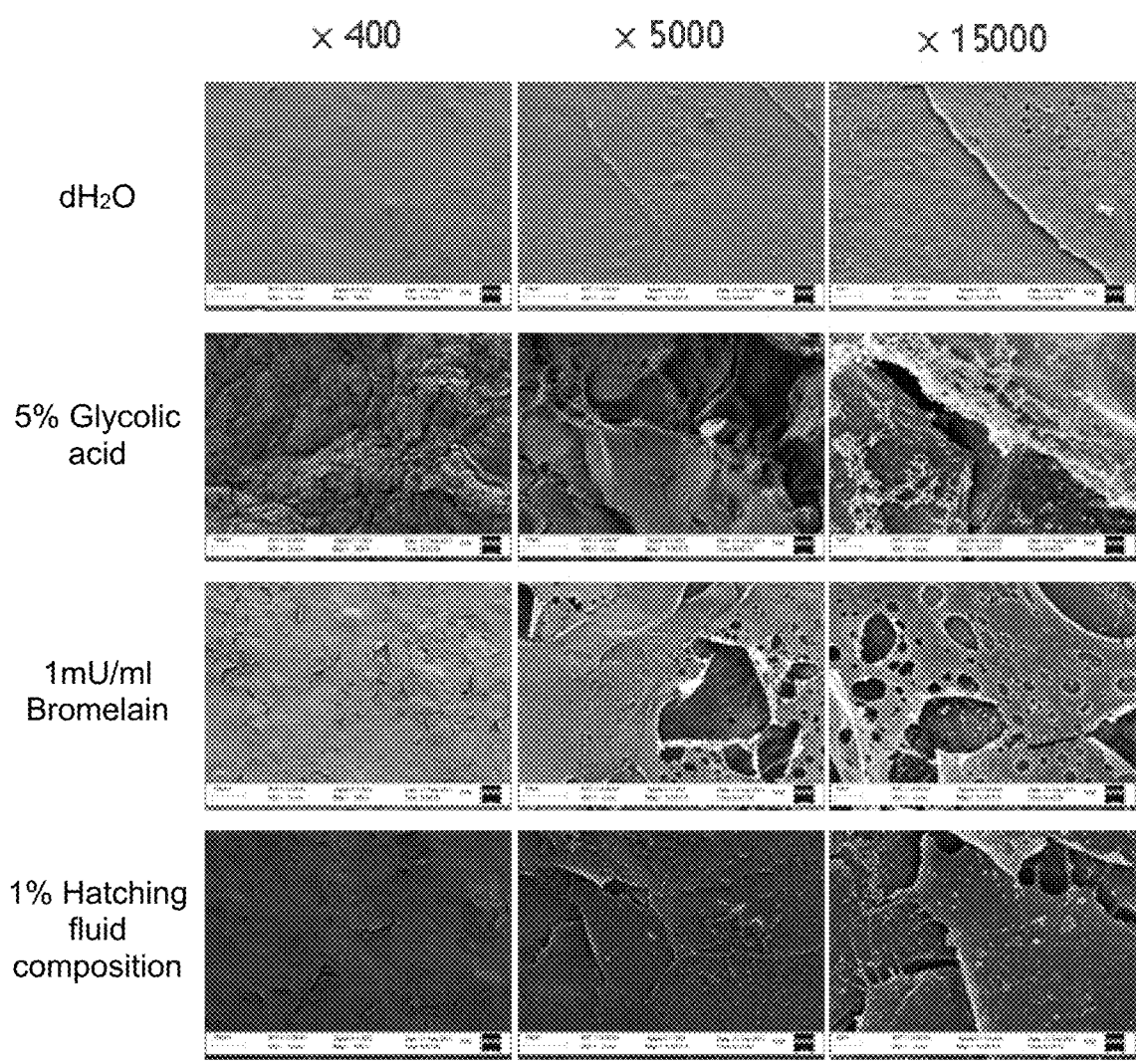
FIG. 5 shows scanning electronmicrographs (×400, ×5000 and ×15000 magnification) of reconstructed human epidermis treated with water, 5% glycolic acid, 1 mU/ml Bromelain or 1% hatching fluid composition for 12 hours.

Evaluation of scanning electronmicrographs of the treated reconstituted human epidermis after 12 hours (FIG. 5) shows that treatment with a 5% solution of glycolic acid results in damaged stratum corneum and skin corrosion. Treatment with Bromelain results in desquamation by digestion of the cells' envelope. In contrast, treatment with the hatching fluid composition of the invention results in desquamation by shedding of intact corneocytes because only the cell binding sites have been degraded. Thus, the hatching fluid solution provides gentle micro-exfoliation of the skin.

Figure 6:
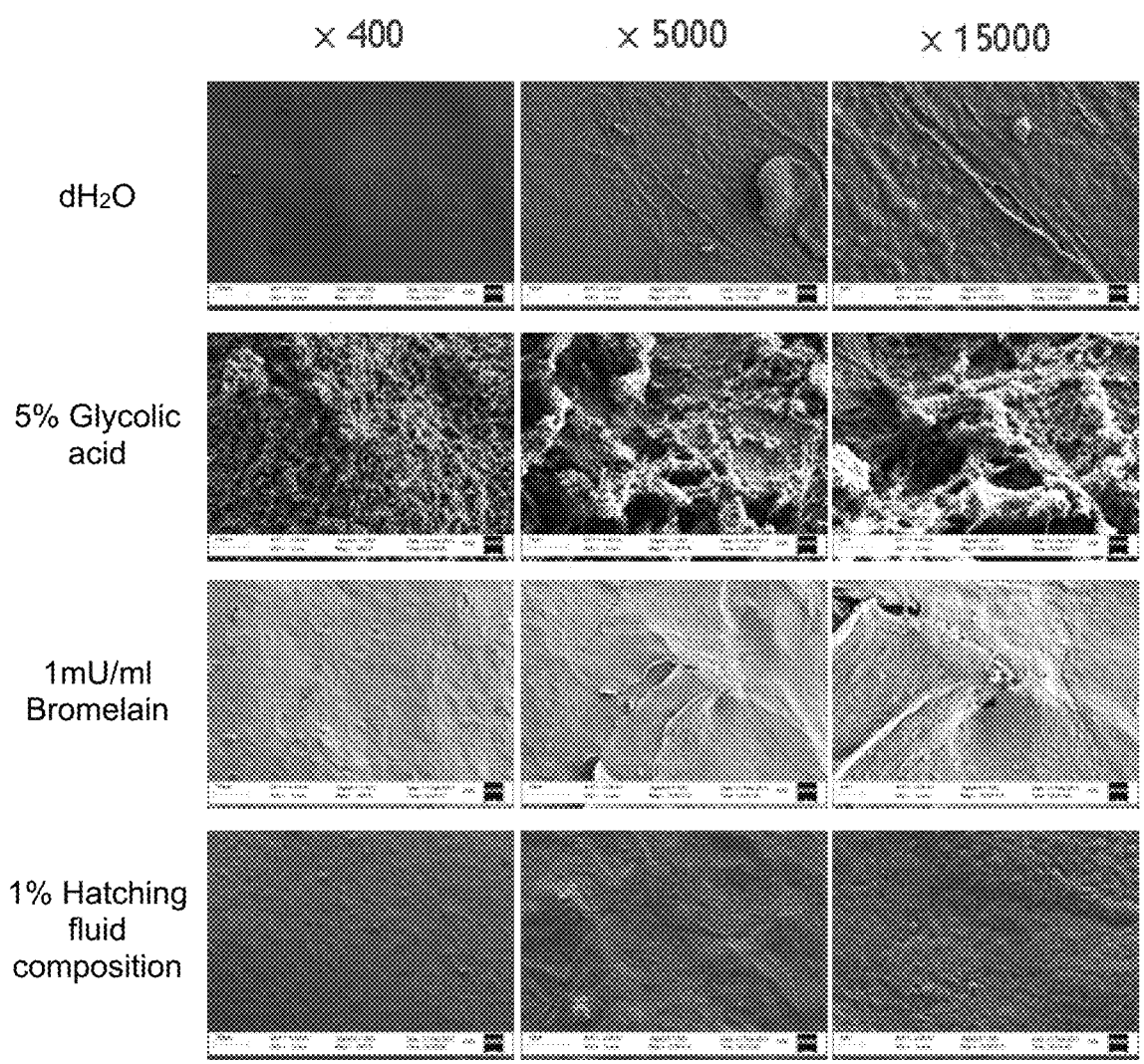
FIG. 6 shows scanning electronmicrographs (×400, ×5000 and ×15000 magnification) of reconstructed human epidermis treated with water, 5% glycolic acid, 1 mU/ml Bromelain or 1% hatching fluid composition for 48 hours.

After exposure for 48 hours, scanning electronmicrographs of the reconstituted human epidermis (FIG. 6) show that glycolic acid results in heavily damaged skin, wherein the cell envelope has been broken and the cell cytoskeleton is clearly visible. Whilst treatment with Bromelain results in a fairly smooth skin surface, there is still evidence of rough patches. However, treatment with the hatching fluid composition of the invention results in an ultra smooth skin surface that is better than control (i.e. untreated) skin. Thus, the hatching fluid composition may be viewed as providing a skin smoothing effect.

Figure 7:
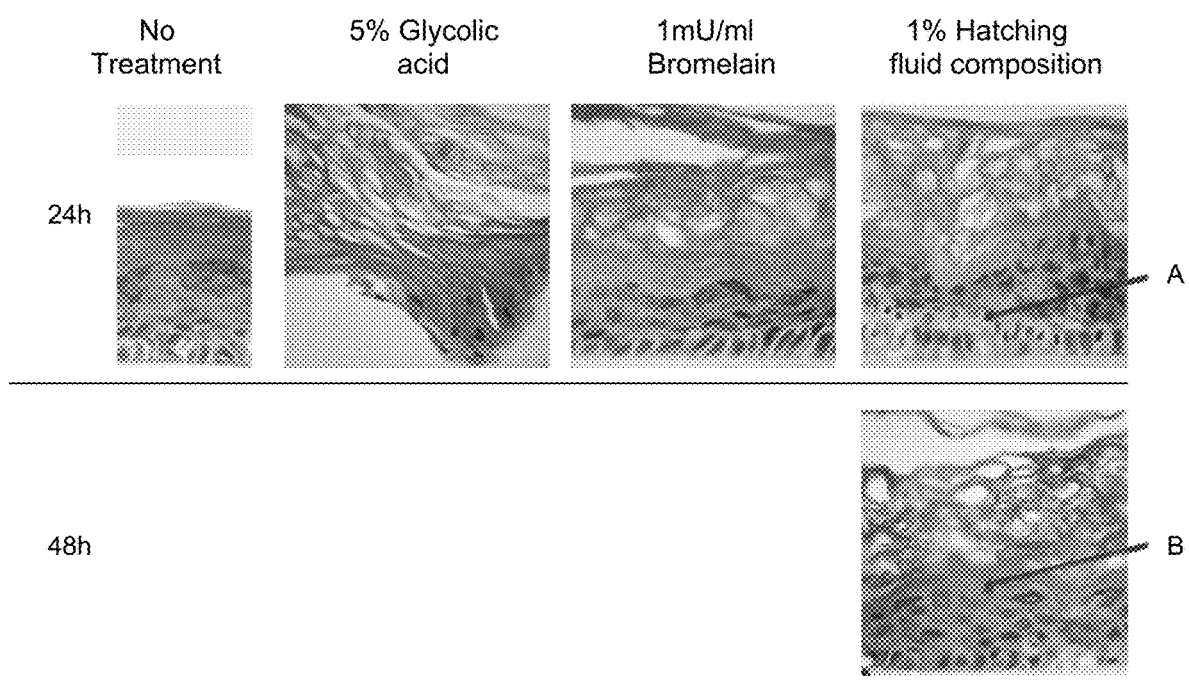
FIG. 7 shows light micrographs of sections of reconstructed human epidermis untreated or treated with 5% glycolic acid, 1 mU/ml Bromelain or 1% hatching fluid composition for 12 or 24 hours. Arrow (A) shows cell proliferation and differentiation and arrow (B) shows denser stratum granulosum and a higher concentration of lamellar granules.

Light microscopy of sections of reconstructed human epidermis (FIG. 7) shows that exposure to glycolic acid for 24 hours results in the destruction living cells, including epidermal stem cells from the stratum basale. All that remains following treatment with glycolic acid are a few pyknotic nuclei (where the chromatin has condensed irreversibly) and anucleated cells. Exposure to Bromelain for 24 hours results in minimal alterations to the stratum basale and the stratum spinosum. In contrast, after exposure to the hatching fluid composition of the invention for 24 hours the reconstructed skin shows evidence of cell proliferation and differentiation (see arrow A of FIG. 7). After 48 hours of exposure to the hatching fluid composition the skin shows evidence of a denser stratum granulosum and a higher concentration of lamellar granules (see arrow B of FIG. 7). Thus the hatching fluid composition of the invention has a skin rejuvenating effect and results in an improvement of skin barrier function.

The invention claimed is:

1. A cosmetic composition comprising polypeptides from Salmonidae eggs obtained by a method comprising the steps of:
   a) suspending Salmonidae eggs in water;
   b) inducing synchronized hatching of said eggs;
   c) filtering the hatched eggs to obtain hatching fluid; and
   d) filtering the hatching fluid from step c), wherein the step of filtering the hatching fluid comprises the steps of:
      (i) filtering the hatching fluid using a filter with a pore size of at least 5 µm, and collecting the filtrate;
      (ii) filtering the filtrate from step (i) using a filter with a pore size of 0.30-0.60 µm, and collecting the filtrate;
      (iii) exchanging water in the filtrate from step (ii) with a pharmaceutically acceptable buffer by performing diafiltration using a filter with an exclusion size of less than 15 kDa to obtain a filtrate solution;
      (iv) filtering the filtrate solution from step (iii) using a filter with a pore size of 0.15-0.30 µm, and collecting the filtrate;
      (v) preparing a cosmetic composition from the filtrate from step (iv), wherein the filtrate from step (iv) is substantially free of components derived from the Salmonidae eggs other than polypeptides or portions thereof.

2. The composition of claim 1, wherein the composition comprises 0.1-5% volume of the filtrate from step (iv) per unit volume of cosmetic composition.

3. The composition of claim 1, wherein the filtrate from step (iv) has an enzymatic activity of 1000-10000 mU/L, measured by the capacity of the solution to cleave the Factor Xa chromogenic substrate ($CH_3OCO$-D-CHA-Gly-Arg-pNA-AcOH).

4. The composition of claim 1, wherein the filtrate from step (iv) has an enzymatic activity of 3000-6000 mU/L, measured by the capacity of the solution to cleave the Factor Xa chromogenic substrate ($CH_3OCO$-D-CHA-Gly-Arg-pNA-AcOH).

5. The composition of claim 1, wherein the composition further comprises one or more pharmaceutically acceptable excipients, pharmaceutically acceptable diluents or pharmaceutically acceptable active components.

6. The composition of claim 5, wherein the pharmaceutically acceptable active components promote the aesthetic appearance of skin.

7. The composition of claim 5, wherein the pharmaceutically acceptable active components are selected from minerals, vitamins, enzymes, proteins, peptides, amino acids, lipids, antioxidants, polysaccharides, substances suitable as sunscreen filters, chemical exfoliants, extracts, and mixtures thereof.

8. The composition of claim 1, wherein the composition comprises a stabilizing agent that stabilizes the polypeptides against degradation.

9. The composition of claim 1, wherein the method from which the composition is obtained further comprises repeating the diafiltration step of step (iii).

10. The composition of claim 1, wherein the method from which the composition is obtained further comprises diluting the filtrate solution from step (iii) or the filtrate from step (iv).

11. The composition of claim 1, wherein the exclusion size of the filter in step (iii) is less than 10 kDa.

12. The composition of claim 1, wherein the Salmonidae eggs are from Atlantic salmon or Pacific salmon.

13. A product, material or device coated or impregnated with or chemically bonded to the composition of claim 1.

14. A method for improving the cosmetic appearance of skin of a mammalian animal comprising topically administering the cosmetic composition of claim 1 to the skin of said mammalian animal.

15. The method of claim 14, wherein improving the cosmetic appearance of skin of a mammalian animal comprises reducing the cosmetic appearance or prevalence of wrinkles, fine lines, hyperpigmentation, laxity, dry skin, scaling and/or transepidermal water loss in skin having wrinkles, fine lines, hyperpigmentation, laxity, dry skin, scaling and/or transepidermal water loss.

16. The method of claim 15, wherein administering the cosmetic composition results in a reduction in the number and/or size of skin wrinkles and/or fine lines and/or a reduction in skin laxity.

17. The method of claim 15, wherein administering the cosmetic composition moisturizes the skin thereby reducing the cosmetic appearance or prevalence of dry skin, scaling and/or transepidermal water loss.

18. The method of claim 15, wherein administering the cosmetic composition results in a reduction in the pigmentation of hyperpigmented skin.

19. The method of claim 14, wherein the skin is aged skin.

20. A method of treating dermatoheliosis in a mammalian animal in need thereof, comprising topically administering the cosmetic composition of claim 1 to the skin of said animal.

* * * * *